US005639275A

United States Patent [19]
Baetge et al.

[11] Patent Number: 5,639,275
[45] Date of Patent: Jun. 17, 1997

[54] DELIVERY OF BIOLOGICALLY ACTIVE MOLECULES USING CELLS CONTAINED IN BIOCOMPATIBLE IMMUNOISOLATORY CAPSULES

[75] Inventors: Edward E. Baetge; Joseph P. Hammang, both of Barrington; Frank T. Gentile, Warwick; Mark D. Lindner, Bristol; Shelley R. Winn, Smithfield; Dwaine F. Emerich, Providence, all of R.I.

[73] Assignee: CytoTherapeutics, Inc., Providence, R.I.

[21] Appl. No.: 449,756

[22] Filed: May 25, 1995

Related U.S. Application Data

[63] Continuation-in-part of Ser. No. 105,278, Aug. 12, 1993, abandoned.

[51] Int. Cl.$^6$ .............................. A61K 9/22; C12N 15/00; C12N 5/00; A01N 63/00
[52] U.S. Cl. .................. 604/891.1; 424/422; 424/424; 424/93.1; 424/93.2; 435/172.3; 435/240.2
[58] Field of Search .............................. 424/93.21, 408; 604/891.1

[56] References Cited

U.S. PATENT DOCUMENTS

| | | |
|---|---|---|
| 3,093,831 | 6/1963 | Jordan . |
| 3,615,024 | 10/1971 | Michaels . |
| 4,298,002 | 11/1981 | Ronel et al. . |
| 4,352,883 | 10/1982 | Lim . |
| 4,353,888 | 10/1982 | Sefton . |
| 4,409,331 | 10/1983 | Lim . |
| 4,470,461 | 9/1984 | Kaufman et al. . |
| 4,686,098 | 8/1987 | Kopchick et al. . |
| 4,689,293 | 8/1987 | Goosen et al. . |
| 4,749,620 | 6/1988 | Rha et al. . |
| 4,753,635 | 6/1988 | Sagen et al. . |
| 4,789,550 | 12/1988 | Hommel et al. . |
| 4,806,355 | 2/1989 | Goosen . |
| 4,868,121 | 9/1989 | Scharp et al. . |
| 4,883,666 | 11/1989 | Sabel et al. . |
| 4,892,538 | 1/1990 | Aebischer et al. . |
| 4,902,295 | 2/1990 | Walthall et al. . |
| 4,942,129 | 7/1990 | Goosen et al. . |
| 5,002,661 | 3/1991 | Chick et al. . |
| 5,026,365 | 6/1991 | Rossini et al. . |
| 5,049,493 | 9/1991 | Khosla et al. . |
| 5,082,670 | 1/1992 | Gage et al. . |
| 5,084,350 | 1/1992 | Chang et al. . |
| 5,106,627 | 4/1992 | Aebischer et al. . |
| 5,122,464 | 6/1992 | Wilson et al. . |
| 5,167,762 | 12/1992 | Carr et al. . |

FOREIGN PATENT DOCUMENTS

| | | |
|---|---|---|
| 127989 | 12/1984 | European Pat. Off. . |
| 161640 | 11/1985 | European Pat. Off. . |
| 188309 | 7/1986 | European Pat. Off. . |
| 301777 | 2/1989 | European Pat. Off. . |
| 338841 | 10/1989 | European Pat. Off. . |
| 2094833 | 9/1982 | United Kingdom . |
| WO84/01287 | 4/1984 | WIPO .............. A61K 9/48 |
| WO89/04655 | 6/1989 | WIPO . |
| WO91/09119 | 6/1991 | WIPO . |
| WO91/07951 | 6/1991 | WIPO . |
| 9110470 | 7/1991 | WIPO . |
| WO91/10470 | 7/1991 | WIPO . |
| WO91/10425 | 7/1991 | WIPO . |
| WO92/19195 | 11/1992 | WIPO . |
| 9219195 | 11/1992 | WIPO . |
| WO93/00439 | 1/1993 | WIPO . |
| WO93/02635 | 2/1993 | WIPO . |

OTHER PUBLICATIONS

Emerich et al. Cell Transpl. vol. 1, CT 126, 1992.
Cabasso in Encyl. of Chemical Technology 12:492, 1980.
Lacy et al. Science 254:1782, 1991.
Aebischer et al., *Biomaterials*, 12, 50–56 (1991).
Algire et al., *J. National Cancer Institute*, 15, 493–506 (1954).
Altman, *Trans. Am. Soc. Artif. Intern. Organs*, vol. XXX, 382–386 (1984).
Altman et al., *Diabetes*, 35, 625–633 (1986).
Archer et al., *J. Surgical Research*, 28, 77–85 (1980).
Backman et al., *Psychol. Aging*, 6, 489–492 (1991).
Baetge et al., *PNAS*, 85, 3648–3652 (1988).
Baetge et al., *PNAS*, 83, 5454–5458 (1986).
Bartus et al., *Science*, 217, 408–417 (1982).
Bartus, *Treatment Development Strategies For Alzheimer's Disease*, Mark Powley Associates (T. Crook, ed.), Ch. 2, 15–33.
Beal et al., *J. Neurosci.*, 8, 3901–3908 (1988).
Beal, *Synapse*, 3, 38–47 (1989).
Besnard et al., *J. Biol. Chem.*, 266, 18877–18883 (1991).
Bontempo et al., *Blood*, 69, 1721–1724 (1987).
Britt et al., *Diabetes*, 30, 580–583 (1981). Please note that the volume and page numbers for this document were incorrectly typed in the specification. This citation stands corrected above.

(List continued on next page.)

*Primary Examiner*—Suzanne E. Ziska
*Attorney, Agent, or Firm*—Fish & Neave; Ivor R. Elrifi; Petrina S. Hsi

[57] ABSTRACT

This invention provides improved devices and methods for long-term, stable expression of a biologically active molecule using a biocompatible capsule containing genetically engineered cells for the effective delivery of biologically active molecules to effect or enhance a biological function within a mammalian host. The novel capsules of this invention are biocompatible and are easily retrievable. This invention specifically provides improved methods and compositions which utilize cells transfected with recombinant DNA molecules comprising DNA sequences coding for biologically active molecules operatively linked to promoters that are not subject to down regulation in vivo upon implantation into a mammalian host. Furthermore, the methods of this invention allow for the long-term, stable and efficacious delivery of biologically active molecules from living cells to specific sites within a given mammal. In addition, this invention provides a general means for maintaining, for extended periods of time, the in vivo expression of transgenes.

6 Claims, 8 Drawing Sheets

OTHER PUBLICATIONS

Burgess et al., *Ann. Rev. Biochem*, 58, 575–606 (1989).
Cabasso, I., *Encyclopedia of Chemical Technology*, 12, 492–517 (1980).
Cai et al., *Artificial Organs*, 12(5), 388–393 (1988).
Cepko, *Neuron*, 1, 345–353 (1988).
Chang et al., *Human Gene Therapy*, 4, 433–440 (1993).
Christenson, Ph.D. Thesis, Brown University (1990). Please note that the year of this thesis was incorrectly stated in the specification. This citation stands corrected above.
Christenson et al., *J. Biomed. Mat. Res.*, 23, 705–718 (1989).
Cohen et al., *J. Am. Chem. Soc.*, 112, 7832–7833 (1990).
Cole et al., *Diabetologia*, 35, 231–237 (1992).
Colton et al., *The Kidney*, W.B. Saunders Co. (B.M. Brenner and F.C. Rector, eds.), 2425–89 (1981).
Darquy et al., *Trans. Am. Soc. Artif. Intern. Organs*, vol. XXXIII, 356–358 (1987).
Darquy et al., *Diabetologia*, 28, 776–780 (1985).
Dionne et al., *ASAIO Abstracts*, 99 (1993).
Dionne, Ph.D. Thesis, Massachusetts Institute of Technology, 170–184 (1989).
Dupuy et al., *J. Biomed. Mat. Res.*, 22, 1061–1070 (1988).
Edmunds et al., *Applied Biochemistry and Biotechnology*, vol. 20/21, 603–619 (1989).
Emerich et al., *Neuromethods 21, Animal Models of Neurological Disease*, 65–134 (1992).
Emerich et al., *Cell Transplantation*, vol. 1, 1–27 (1992).
Emerich et al., *Neuroscience and Biobehavioral Reviews*, 16, 437–447 (1992).
Faithfull, *Anaesthesia*, 42, 234–242 (1987).
Fan et al., *Diabetes*, 39, 519–522 (1990).
Folstein et al., *J. Psychiat. Res.*, 12, 189–198 (1975).
Foster et al., *Brain Res.*, 336, 207–214 (1985).
Frim et al., *NeuroReport*, vol. 4, 367–370 (1993).
Fu et al., *Transplantation*, 47, 432–435 (1989).
Gordon et al., *Nature*, 326, 403–405 (1987).
Gritz et al., *Gene*, vol. 25, 179–188 (1983).
Grulke, *Polymer Handbook*, 3rd Ed., John Wiley & Sons (J. Brandrup and E.H. Immergut, eds.), Ch. 7, pp. 519–520.
Herscovitch et al., *J. Cereb. Blood Flow Metab*, 7, 527–542 (1987).
Hoffman et al., *Exp. Neurology*, 122, 100–106 (1993).
Hoffman, Ph.D. Thesis, Univ. Rochester, Division of Biology and Medicine (1993).
Hoyle et al., *Neuron*, 10, 1019–1034 (1993).
Iwata et al., *Diabetes*, 38, 224–225 (1989); discloses islets microencapsulated in agarose gel.
Jarret et al., *Lancet*, (2), 1009–1012 (1976).
Jolley et al., *Transplantation Proceedings*, vol. IX, 363–365 (1977).
Kaneda, et al., *Neuron*, 6, 583–594 (1991).
Klomp, *Journal of Biomedical Materials Research*, 17, 865–871 (1983).
Koliatsos et al., *Experimental Neurology*, 112, 161–173 (1991).
Koliatsos et al., *Annals of Neurology*, 30, 831–840 (1991).
Kordower et al., *J. Comp. Neurol*, 298, 443–457 (1990).
Kromer, *Science*, 235, 214–216 (1986).
Lacy et al., *Science*, 204, 312–313 (1979).
Lacy et al., *Science*, 254, 1782–1784 (1991).
Land et al., *Nature*, 304, 596–602 (1983).
Lemke et al., *Neuron*, 1, 73–83, (1988).
Leung et al., *Artificial Organs*, 7, 208–212 (1983).
Lim et al., *Science*, 210, 908–910 (1980).
Liu et al., *Human Gene Therapy*, 4, 291–301 (1993).
Livett, *Physiological Reviews*, 64, 1103–1161 (1984).
Matthews et al., *Recent Advances in Germfree Research*, Tokai Univ. Press, 61–64 (1981).
Maysinger et al., *Neurochem. Int.*, 23, No. 2, 123–129 (1993).
Mercer et al., *Neuron*, 7, 703–716 (1991).
Miniats et al., *Can. J. Comp. Med.*, 42, 428–437 (1978).
Nakahira et al., *J. Biol. Chem.*, 265, 19786–19791 (1990).
NASA *Tech. Briefs* NPO–17517, vol. 15, #1, Item #113, pp. i, 1, 1a and 1b–29b (1991).
Nordberg et al., *Neuroscience Lett.*, 72, 115–119 (1986).
O'Shea et al., *Diabetes*, 35, 943–946 (1986).
O'Shea et al., *Biochimica et Biophysica Acta*, 804, 133–136 (1984).
Olson et al., *J. Neural Transmission*, 4, 79–95 (1992).
Olson, *Proceedings of the Xth Meeting of the World Society for Stereotactic and Functional Neurosurgery*, pp. 250–267 (1990).
Palmiter et al., *PNAS*, 88, 478–482 (1991).
Piccardo et al., *Neuro Report*, 3, 353–356 (1992).
Rabizadeh et al., *Science*, 261, 345–348 (1993).
Ray et al., *PNAS*, 90, 3602–3606 (1993).
Reach, *Biomed. Biochim. Acta*, 43, 569–576 (1984).
Richards et al., *PNAS*, 89, 8591–8595 (1992).
Ricordi et al., *Transplantation*, 45(6), 1148–1151 (1988).
Roberts et al., *Synapse*, 3, 363–371 (1989).
Ronel et al., *Journal of Biomedical Materials Research* 17, 855–864 (1983).
Rosenberg et al., *Science*, 242, 1575–1578 (1988).
Sakimura et al., *Gene*, 60, 103–113, (1987).
Sanberg et al., *Exp. Neurol.*, 66, 444–466 (1979).
Sanberg et al., *Med. J. Aust.*, 1, 407–409 (1981).
Scharp et al., *World J. Surg.*, 8, 221–229 (1984).
Schinstine et al., *Molecular and Cellular Approaches for the Treatment of Neurological Disease*, (S.G. Waxman, ed.), Raven Press, Ch. 16, 311–323 (1993).
Schwarcz et al., *Neurosci. Lett.*, 38, 85–90 (1983).
Schwarcz et al., *Science*, 219, 316–318 (1983).
Schweitzer et al., *J. Cell Biol.*, 101, 667–676 (1985).
Short et al., *Dev. Neurosci.*, 12, 34–45 (1990).
Soeldner et al., *Diabetes*, 14, 771–779 (1965).
Soon-Shiong et al., *Proc. Natl. Acad. Sci. USA*, 90, 5843–5847 (1993).
Southern et al., *J. Mol. Appl. Genet.*, 1, 327–341 (1982).
Southern, *In Vitro*, 18, 315 (1981).
Springer, *DN&P*, 4(7), 394–399 (1991).
Stowell et al., *Biochem. J.*, 276, 349–355 (1991).
Sugamori et al., *Trans. Am. Soc. Artif. Intern. Organs* vol. XXXV, 791–799 (1989).
Sun et al. *CRC Critical Reviews in Therapeutic Carrier Systems*, 4, 1–12 (1987).
Sun, *Methods in Enzymology*, 137, 575–580 (1988).
Sun, *Trans. Am. Soc. Artif. Intern. Organs*, vol. XXXIII, 787–790 (1987).
Sun et al., *Biomat., Art. Cells, Art. Org.*, 15, 483–496 (1987).
Sun et al., *Trans. Am. Soc. Artif. Intern. Organs*, vol. XXXII, 39–41 (1986).
Sun, *Applied Biochemistry and Biotechnology*, 10, 87–99 (1984).
Sun et al., *Diabetes*, 26, 1136–1139 (1977).
Tresco et al., *Cell Transplantation*, 1, 255–264 (1992).
Tze et al., *Transplantation*, 33, 563–564 (1982).
Tze et al., *Diabetologia*, 16, 247–252 (1979).

Van Ooteghem et al., *Brain Res. Bull.*, 12, 543–553 (1984).
Weber et al., *Transplantation*, 49, 396–404 (1990).
Will et al., *Behav. Brain Res.*, 17, 17–24 (1985).
Wilson et al., *J. Biol. Chem.* 263, 2712–2718 (1988).
Winn et al., *J. Biomed. Materials Res.*, 23, 31–44 (1989).
Winn et al., *Proc. Natl. Acad. Sci. USA*, 91, No. 6, 2324–2328 (1994).
Wu et al., *Trans. Am. Soc. Artif. Intern. Organs*, vol. XXXV, 736–738 (1989).
Wu et al., *International Journal of Pancreatology*, 3, 91–100 (1988).

DELIVERY OF BIOLOGICALLY ACTIVE MOLECULES USING CELLS CONTAINED IN BIOCOMPATIBLE IMMUNOISOLATORY CAPSULES

CROSS-REFERENCE TO RELATED APPLICATIONS

This is a continuation-in-part of copending patent Cooperation Treaty application Ser. No. PCT/US/94/09299, filed Aug. 12, 1994, which is a continuation-in-part of U.S. application Ser. No. 08/105,278, filed Aug. 12, 1993, now abandoned.

TECHNICAL FIELD OF THE INVENTION

The present invention relates to improved biocompatible capsules for delivery of biologically active molecules to a host. In particular, these improved capsules have an outer surface morphology characterized by a specific macropore distribution and macropore size range. In addition, the present invention relates to improved devices and methods for the long-term, stable expression of biologically active molecules and the delivery of those biologically active molecules and in particular the use of genetically altered cells contained in biocompatible immunoisolatory capsules to achieve such expression and delivery.

BACKGROUND OF THE INVENTION

Many clinical conditions, deficiencies, and disease states can be remedied or alleviated by supplying to the patient a factor or factors produced by living cells or removing from the patient deleterious factors which are metabolized by living cells. In many cases, these factors can restore or compensate for the impairment or loss of organ or tissue function. Examples of disease or deficiency states whose etiologies include loss of secretory organ or tissue function include (a) diabetes, wherein the production of insulin by pancreatic islets of Langerhans is impaired or lost; (b) hypoparathyroidism, wherein the loss of production of parathyroid hormone causes serum calcium levels to drop, resulting in severe muscular tetany; (c) Parkinsonism, wherein dopamine production is diminished; and (d) anemia, which is characterized by the loss of production of red blood cells secondary to a deficiency in erythropoietin. The impairment or loss of organ or tissue function may result in the loss of additional metabolic functions. For example, in fulminant hepatic failure, liver tissue is rendered incapable of removing toxins, excreting the products of cell metabolism, and secreting essential products, such as albumin and Factor VIII. Bontempo, F. A., et al, (1987) *Blood*, 69, pp. 1721–1724.

In other cases, these factors are biological response modifiers, such as lymphokines or cytokines, which enhance the patient's immune system or act as anti-inflammatory agents. These can be particularly useful in individuals with a chronic parasitic or infectious disease, and may also be useful for the treatment of certain cancers.

It may also be desirable to supply trophic factors to a patient, such as nerve growth factor (NGF), brain-derived neurotrophic factor (BDNF), neurotrophin-3 (NT-3), neurotrophin-4/5 (NT-4/5), ciliary neurotrophic factor (CNTF), glial cell line-derived neurotrophic factor (GDNF), cholinergic differentiation factor/Leukemia inhibitory factor (CDF/LIF), epidermal growth factor (EGF), insulin-like growth factor (IGF), basic fibroblast growth factor (bFGF), platelet-derived growth factor (PDGF) and the like.

In many disease or deficiency states, the affected organ or tissue is one which normally functions in a manner responsive to fluctuations in the levels of specific metabolites, thereby maintaining homeostasis. For example, the neurons of the hippocampus produce high levels of NGF which is directly supportive of the basal forebrain cholinergic neurons which innervate the hippocampus. A decrease in the level of NGF produced by these neurons may result in the loss of cholinergic input to this vital structure, resulting in age-associated memory impairment found in Alzheimer's disease.

In the nervous system, chronic, low-level delivery of trophic factors is sufficient to maintain the health of growth-factor dependent cell populations. In chronic disorders such as Alzheimer's disease and Huntington's disease, long-term delivery of one or more neurotrophic factors such as NGF, BDNF, NT-3, NT-4/5, CNTF, GDNF and CDF/LIF may be required to maintain neuronal viability. These growth factors cannot be delivered through systemic administration as they are unable to traverse the blood-brain barrier. Therefore, these neurotrophic factors must be delivered directly into the central nervous system (CNS).

Many investigators have attempted to reconstitute, augment, or replace organ or tissue function by transplanting whole organs, organ tissue, or cells which provide secreted products or affect metabolic functions. Moreover, transplantation can provide dramatic benefits but is limited in its application by the relatively small number of organs suitable and available for grafting. In general, the patient must be immunosuppressed in order to avert immunological rejection of the transplant, which generally results in loss of transplant function and eventual necrosis of the transplanted tissue or cells. In many cases, however, it is desireable for the transplant to remain functional for a long period of time, even for the remainder of the patient's lifetime. It is both undesirable and expensive to maintain a patient in an immunosuppressed state for a substantial period of time.

Another approach used in transplantation procedures is the implantation of cells or tissues within a semi-permeable physical barrier which will allow diffusion of nutrients, waste materials, and secreted products, but minimize the deleterious effects of the cellular and molecular effectors of immunological rejection. A variety of devices or capsules which protect tissues or cells producing a selected product from the immune system have been explored. These include extravascular diffusion chambers, intravascular diffusion chambers, intravascular ultrafiltration chambers, and implantation of microencapsulated cells (Scharp, *World J. Surg.*, 8, pp. 221–9 (1984)). These devices were envisioned as providing a significant advance in the field of transplantation, as they would alleviate the need to maintain the patient in an immunosuppressed state, and would thereby allow many more patients to receive restorative or otherwise beneficial transplants by allowing the use of donor cells or tissue which could not have been used with the conventional transplantation techniques.

The use of encapsulated cells hinders elements of the immune system from entering the capsule, thereby protecting the encapsulated cells from immune destruction. This technology increases the diversity of cell types that can be employed in therapy. The semipermeable nature of the capsule membrane also permits the molecule of interest to easily diffuse from the capsule into the surrounding host tissue. This technique prevents the inherent risk of tumor formation and allows the use of unmatched human or even animal tissue, without immunosuppression of the recipient. Moreover, the implant may be retrieved if necessary or desired. Such retrievability may be essential in many clinical situations.

The outer surface morphology may affect a variety of parameters including the strength of the capsule, the retrievability of the capsule, as well as the ability of the capsule to support viable cells for extended periods of time.

It is desirable to provide capsules that permit viability of the encapsulated cells for extended periods of time and that are more easily retrievable without breakage.

Numerous encapsulation devices are known, having various outer surface morphologies. Capsules have been categorized as Type 1 (T1), Type 2 (T2) or Type 4 (T4) depending on their outer surface morphology. Such membranes are described, e.g., in Lacy et al., "Maintenance Of Normoglycemia In Diabetic Mice By Subcutaneous Xenografts Of Encapsulated Islets", Science, 254, pp. 1782–84 (1991) and Dionne et al., PCT/US92/03327. The novel membranes of this invention have been designated T1/2, and are characterized by a hybrid outer surface morphology wherein the total area occupied by macropores, as well as the macropore diameter fall within a selected range.

The use of dividing cells and cell lines to provide the needed biological function offers a number of significant advantages over fully differentiated tissue and/or organs. Cells may be grown to large numbers in vitro and can be banked and screened for pathogens. Additionally, cells and cell-lines are more amenable to genetic engineering than primary organs, or tissues. The ability to introduce heterologous recombinant DNA allows many new possibilities for the alteration of the function or phenotype of cells to be transplanted. This in turn provides for a greater diversity of therapeutic uses for transplanted cells.

Retroviral vectors have generally been employed to genetically alter the cells used in such procedures (Gage et al., U.S. Pat. No. 5,082,670). However, it is known that retroviral expression vectors do not provide high-level long-term in vivo expression of heterologous proteins. A variety of factors contribute to the observed down-regulation of transgene expression under the control of retroviral promoters. These factors include quiescence of the genetically altered cells, methylation of CpG doublets within the promoters, and removal of selection pressure. Most expression vectors driven by mammalian promoters are also not best suited for traditional transplantation paradigms because of their inherent low-level promoter activity (See M. Schinstine and F. Gage, Molecular and Cellular Approaches for the Treatment of Neurological Disease, S. G. Waxman, ed., Raven Press pp. 311–323 (1993)).

In addition to the problem of down regulation of retroviral promoters in the CNS, there are other disadvantages in using retroviruses for gene therapy. For example, there is a serious concern about the possibility for recombination events occurring within a transplanted mammalian host previously exposed to or currently infected with virus containing genetic elements which may result in the conversion of replication-defective virus to live virus. In addition, working with infectious virus particles poses safety risks for the laboratory workers and medical practitioners producing and administering the reagent. Finally, these concerns have led to a heightened perception of risk among researchers and medical practitioners as well as regulatory authorities.

Although genetically engineered cells have been transplanted in vitro both in encapsulated and unencapsulated form, long-term, stable expression of the heterologous DNA has not been satisfactorily achieved. For example, a recently published study (Hoffman et al., Experimental Neurology, 122, pp. 100–106 (August, 1993)) refers to the use of encapsulated, allogeneic cells genetically engineered to secrete mouse-NGF for the delivery of NGF to the central nervous system (CNS) of rats. The NGF gene expression in the described system was under the control of a retroviral promoter. As described above, retroviral vectors do not give rise to long-term, stable expression of transgenes in vivo. Accordingly, the method reported in that study will not be suitable for long-term therapeutic applications.

Accordingly, a method of delivering appropriate quantities of needed substances, such as growth factors, enzymes and hormones, from genetically altered cells, for an extended period of time is still unavailable and would be very advantageous to those in need of long-term treatment. Moreover, methods for maintaining the long term, stable in vivo expression of transgenes in transplanted cells are also unavailable and are needed (for example, see Schinstine and Gage (1993), supra, at p. 321).

Therefore, the need remains for devices and delivery methods which incorporate genetically altered cells that facilitate long-term, stable transgene expression in vivo.

SUMMARY OF THE INVENTION

The present invention provides novel T1/2 hybrid capsules that may permit viability of encapsulated cells for an extended period of time upon implantation in a host mammal, and that are more easily retrievable.

The present invention provides devices and methods for long-term, stable expression of a biologically active molecule using a biocompatible capsule containing genetically engineered cells for the effective delivery of biologically active molecules to effect or enhance a biological function within a mammalian host. This invention specifically provides improved methods and compositions which utilize cells transfected with recombinant DNA molecules comprising DNA sequences coding for biologically active molecules operatively linked to promoters that are not subject to down regulation in vivo upon implantation into a mammalian host. Furthermore, the methods of this invention allow for the long-term, stable and efficacious delivery of biologically active molecules from living cells to specific sites within a given mammal. This invention provides a general means for maintaining, for extended periods of time, the in vivo expression of transgenes. In addition, this invention provides devices and methods for treatment of age-related cognitive defects.

Definitions

As used herein "a biocompatible capsule" means that the capsule, upon implantation in a host mammal, does not elicit a detrimental host response sufficient to result in the rejection of the capsule or to render it inoperable, for example through degradation.

As used herein "an immunoisolatory capsule" means that the capsule upon implantation into a mammalian host minimizes the deleterious effects of the host's immune system on the cells within its core.

Biological activity refers to the biologically useful effects of a molecule on a specific cell. As used herein "a biologically active substance" is one which may exert its biological activity within the cell in which it is made (e.g., bcl-2 to prevent apoptosis) or it may be expressed on the cell surface and effect the cell's interactions with other cells or biologically active molecules (e.g., a neurotransmitter receptor or cell adhesion molecule) or it may be released or secreted from the cell in which it is made and exert its effect on a separate target cell (e.g., a neurotransmitter, hormone, growth factor, or cytokine).

Down regulation of a promoter means the reduction in the expression of the product of transgene to a level which leads to a lack of significant biological activity of the transgene product after in vivo implantation. As used herein "a promoter not subject to down regulation" means a promoter which, after in vivo implantation in a mammalian host, drives or continues to drive the expression of transgene at a level which is biologically active.

As used herein "long-term, stable expression of a biologically active molecule" means the continued production of a biologically active molecule at a level sufficient to maintain its useful biological activity for periods greater than one month, preferably greater than three months and most preferably greater than six months.

As used herein, an "aged" individual is an individual in whom neural degeneration has occurred or is occurring, either as a result of the natural aging process, or as a result of a neurodegenerative disorder associated with the natural aging process. Neural degeneration as a result of the natural aging process means loss or decline of neural function compared to a previous state not attributable to a defined clinical abnormality or neurological/neurodegenerative disorder, such as Alzheimer's, Parkinson's or Huntington's.

DETAILED DESCRIPTION OF THE INVENTION

Figure 1:
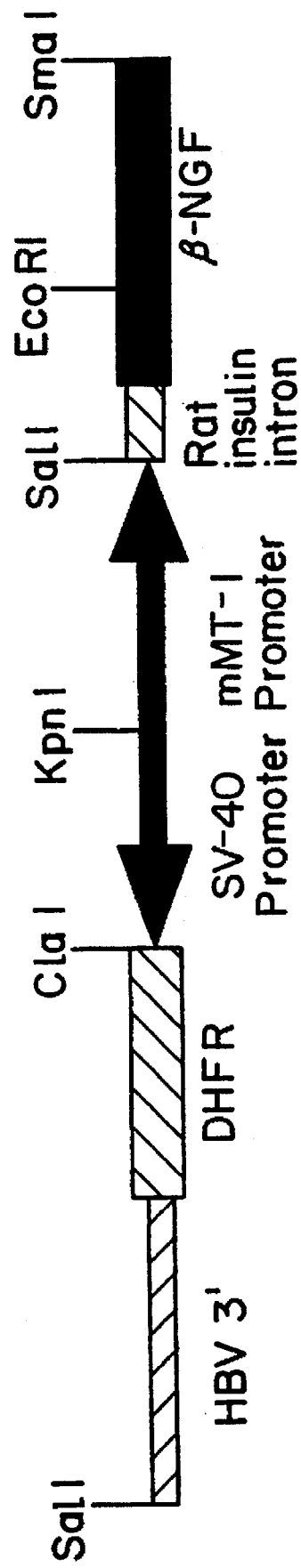
FIG. 1 depicts the restriction map of the pNUT-β-NGF expression vector.

This invention is directed to improved capsules that permit viability of encapsulated cells for an extended period of time and that are easily retrievable. This invention is also directed to improved devices and methods, which use genetically altered cells contained in biocompatible capsules, for the expression of biologically active molecules and long-term, stable delivery of biologically active molecules to host mammals.

The devices and methods of the instant invention are useful for long-term, stable expression of a wide range of biologically active molecules, including high molecular weight products up to 200 kD, to an individual in need of them, and/or to provide needed metabolic functions to an individual, such as the removal of harmful substances. Biologically active molecules used in the devices and methods of the instant invention include a wide variety of factors normally secreted by various organs or tissues. For example, insulin can be delivered to a diabetic patient, dopamine to a patient suffering from Parkinson's disease, Factor VIII to a Type A hemophiliac, or an analgesic to a patient in pain.

Other biologically active molecules which can be used in practicing the instant invention include trophic factors such as erythropoietin, growth hormone, Substance-P, neurotensin, NGF, BDNF, NT-3, NT-4/5, CNTF, GDNF, CDF/LIF, EGF, IGF, PDGF, bFGF, and aFGF.

The devices and methods of the instant invention are also useful for long-term, stable expression of biologically active molecules including hemoglobin, tyrosine hydroxylase, pro-hormone convertase, bcl-2, dopa decarboxylase, and dopamine beta-hydroxylase.

Another family of products suited to delivery by the instant invention comprises biological response modifiers, including lymphokines and cytokines.

The encapsulated cells described herein can also be used to restore or augment vital metabolic functions, such as the removal of toxins or harmful metabolites (e.g., cholesterol) from the bloodstream by cells such as hepatocytes. The methods of the instant invention make possible the implantation of cells without the concomitant need to immunosuppress the recipient for the duration of treatment. Through use of the methods of this invention, homeostasis of particular substances can be restored and maintained for extended periods of time.

The biologically active molecules contemplated within the scope of this invention include molecules that are secreted from the capsule, or from an otherwise transplanted cell, and either directly or indirectly result in a biological effect in the mammalian host, as well as those biologically active molecules that directly or indirectly result in a biological effect on cells contained within the capsule.

A preferred embodiment of this invention is an improved method for delivering neurotrophic factors to the central nervous system (CNS) of host mammals. In a specific embodiment of this invention, an improved method for long-term, stable expression and delivery of nerve growth factor (NGF) to a specific region of the CNS of a mammalian host is provided.

The genes encoding numerous biologically active molecules have been cloned and their nucleotide sequences published. Many of those genes are publicly available from depositories such as the American Type Culture Collection (ATCC) or various commercial sources. Genes encoding the biologically active molecules useful in this invention that are not publicly available may be obtained using standard recombinant DNA methods such as PCR amplification, genomic and cDNA library screening with oligonucleotide probes. Any of the known genes coding for biologically active molecules may be employed in the methods of this invention. See, e.g., U.S. Pat. No. 5,049,493; Gage et al., U.S. Pat. No. 5,082,670; and Genentech U.S. Pat. No. 5,167,762.

Among the genes particularly useful in this invention are the genes encoding human proenkephalin A, human prohormone convertase 2, human prohormone convertase 3, human BDNF, POMC (pro-opiomelanocortin), β-endorphin, prodynorphin, mature human BDNF with the human NGF signal sequence, human CNTF, human NT3, human NGF, rat GDNF, mature human NT5 with the human NGF signal sequence, bovine dopamine β hydroxylase, bovine dopamine decarboxylase, and thymidine kinase.

A gene of interest (i.e., a gene that encodes a suitable biologically active molecule) can be inserted into a cloning site of a suitable expression vector by using standard techniques. It will be appreciated that more than one gene may be inserted into a suitable expression vector. These techniques are well known to those skilled in the art.

The expression vector containing the gene of interest may then be used to transfect the cell line to be used in the methods of this invention. Standard transfection techniques such as calcium phosphate coprecipitation, DEAE-dextran transfection or electroporation may be utilized. Commercially available mammalian transfection kits may be purchased from e.g., Stratagene.

A wide variety of host/expression vector combinations may be used to express the gene encoding the biologically active molecule of interest. Long-term, stable in vivo expression is achieved using expression vectors (i.e., recombinant DNA molecules) in which the gene encoding the biologically active molecule is operatively linked to a promoter that is not subject to down regulation upon implantation in vivo in a mammalian host. Accordingly, such expression vectors would typically not contain a retroviral promoter.

Suitable promoters include, for example, the early and late promoters of SV40 or adenovirus and other known non-retroviral promoters Capable of controlling gene expression.

Useful expression vectors, for example, may consist of segments of chromosomal, non-chromosomal and synthetic DNA sequences, such as various known derivatives of SV40 and known bacterial plasmids, e.g., pUC, pBlue Script™ plasmids from *E. coli* including pBR322, pCR1, pMB9, pUC, pBlue Script™ and their derivatives.

Expression vectors containing the geneticin (G418) or hygromycin drug selection genes (Southern, P. J. (1981), *In Vitro*, 18, p. 315, Southern, P. J. and Berg, P. (1982), *J. Mol. Appl. Genet.*, 1, p. 327) are also useful in practicing this invention. These vectors can employ a variety of different enhancer/promoter regions to drive the expression of both a biologic gene of interest (e.g., NGF) and/or a gene conferring resistance to selection with toxin such as G418 or hygromycin B. The G418 resistance gene codes for aminoglycoside phosphotransferase (APH) which enzymatically inactivates G418 (100–500 μg/μl) added to the culture medium. Only those cells expressing the APH gene will survive drug selection usually resulting in the expression of the second biologic gene as well. The hygromycin B phosphotransferase (HPH) gene codes for an enzyme which specifically modifies hygromycin toxin and inactivates it. Genes cotransfected with or contained on the same plasmid as the hygromycin B phosphotransferase gene will be preferentially expressed in the presence of hygromycin B at 50–200 μg/ml concentrations.

A variety of different mammalian promoters can be employed to direct the expression of the genes for G418 and hygromycin B and/or the biologic gene of interest. These promoters include, but are not limited to, the promoters of hDBH (human dopamine beta hydoxylase) (Mercer et al., *Neuron*, 7, pp. 703–716, (1991)), hTH (human tyrosine hydroxylase) (Kaneda, et al., Neuron, 6, pp. 583–594, (1991)), hPNMT (human phenylethanaolamine N-methyltransferase) (Baetge et al., pNAS, 85, pp. 3648–3652, (1988)), mGFAP (mouse glial fibrillary acidic protein) (Besnard et al., *J. Biol. Chem.*, 266, pp. 18877–18883, (1991)), myelin basic protein (MBP), mNF-L (mouse neurofilament-light subunit) (Nakahira et al., *J. Biol. Chem.*, 265, pp. 19786–19791, (1990)), hPo (human $P_O$, the promoter for the gene encoding the major myelin glycoprotein in the peripheral nervous system) (Lemke et al., *Neuron*, 1, pp. 73–83, (1988)), mMT, rNSE (rat neuron-specific enolase) (Sakimura, et al., *Gene*, 60, pp. 103–113, 1987), and the like.

Examples of expression vectors that can be employed are the commercially available pRC/CMV, pRC/RSV, and pCDAN1NEO (InVitrogen). The viral promoter regions directing the transcription of the drug selection and biologic genes of interest are replaced with one of the above promoter sequences that are not subject to the down regulation experienced by viral promoters within the CNS. For example, the GFAP promoter would be employed for the transfection of astrocytes and astrocyte cell lines, the TH promoter would be used in PC12 cells, or the MBP promoter would be used in oligodendrocytes.

In one embodiment, the pNUT expression vector is used (see FIG. 1). In addition, the pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

A wide variety of cells may be used. These include well known, publicly available immortalized cell lines as well as dividing primary cell cultures. Examples of suitable publicly available cell lines include, baby hamster kidney (BHK), chinese hamster ovary (CHO), mouse fibroblast (L-M), NIH Swiss mouse embryo (NIH/3T3), African green monkey cell lines (including COS-1, COS-7, BSC-1, BSC-40, BMT-10 and Vero), rat adrenal pheochromocytoma (PC12 and PC12A), AT3, rat glial tumor (C6), astrocytes and other fibroblast cell lines. Primary cells that may be used include, bFGF-responsive neural progenitor stem cells derived from the CNS of mammals (Richards et al., *PNAS* 89, pp. 8591–8595 (1992); Ray et al., *PNAS* 90, pp. 3602–3606 (1993)), primary fibroblasts, Schwann cells, astrocytes, β-TC cells, Hep-G2 cells, oligodendrocytes and their precursors, myoblasts and the like.

The cell types that can be employed for encapsulated cell therapy within the scope of this invention include cells from allogeneic and xenogeneic sources. One of the principal advantages of our encapsulated approach rests with the immunoisolatory properties of the membranes of this invention, and their ability to support cells that otherwise would not be appropriate for transplantation (i.e., non-human sources, immortalized and/or tumor cell lines). A particular advantage to using xenogeneic over allogeneic cells is that in the unlikely event of membrane failure, the xenogeneic cells are more likely to be targeted for destruction by the immune system when compared to allogeneic cells. Furthermore, xenogeneic sources are easy to obtain and their use precludes the necessity for the use of human tissue which is difficult to obtain and fraught with societal and ethical considerations. In addition, human tissue may contain adventitious agents that are more readily transmitted to the transplantation recipient. Finally, use of xenogeneic tissue and cell lines for transplantation in humans removes the risks associated with the handling and processing of human tissue.

In one embodiment of the invention, the pNUT amplification expression system is used to transfect BHK cells. However, the pNUT vector containing the gene of interest can also be employed to transfect a large number of other standard immortalized or transformed tissue culture cell lines such as COS, L-cells, CHO, and the like, as discussed above. In addition, the pNUT expression vector can be employed to transfect primary astrocytic, oligodendrocytic or neuronal cell lines (e.g., bFGF-responsive neural progenitor-stem cells, as discussed above).

The cell lines transformed according to this invention are capable of providing long-term, stable expression of a biologically active molecule(s). Such long-term, stable expression can be achieved by increasing or amplifying the copy number of the transgene encoding the biologically active molecule(s), using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841).

Another method for obtaining long-term, stable expression of genes in mammalian cells is by double transfection using two separate drug-selection markers, hygromycin or G418 resistant expression vectors can be employed to sequentially or simultaneously transfect a number of the cell lines above to achieve a variety of gene copy inserts and hence expression levels of the gene of interest.

In one embodiment, cells are transfected with plasmid pRC/CMV containing the coding sequence for the β-NGF or other gene of interest operatively linked to the GFAP promoter/enhancer element replacing the CMV promoter sequences normally found in this expression vector. Upon selection of stable clones expressing the transfected transgene the clones would be retransfected with the same pRc/GFAP NGF expression vector containing the bacterial hygromycin B phosphotransferase gene (Gritz and Davies, *Gene*, pp. 179–188 (1983)) in place of the G418 resistance gene. After stable clones have been reselected in both hygromycin and G418, the cells could be assayed for the clones with the highest number of integrated copies and/or expression of the transfected transgene in both RNA and protein products. In this fashion, other pairs of drug selection expression vectors may be employed to produce cell lines transfected with multiple vectors which have stably integrated high copy numbers of the genetic material and express various levels of biologically active molecules of interest.

A multiplicity of cells may be used in the methods of this invention, such that implantation of a polymer-capsule can be sufficient to provide an effective amount of the needed substance or function to an individual. In addition, more than one biologically active molecule may be stably expressed and/or delivered over long periods from a single capsule.

One way to accomplish this result is to encapsulate a single cell line which has been genetically altered to express more than one heterologous gene.

Another way to accomplish this result is to encapsulate in a single capsule a mixture of cells, wherein some cells have been genetically modified to express one biologically active molecule and other cells have been genetically modified to express a second biologically active molecule. It will be appreciated that a non-genetically engineered cell line can be utilized to provide the second biologically active molecule.

For example, a cell line may also be genetically engineered to express different biologically active molecules. The sub clones of the parental cell lines, each expressing a different transgene, may then be pooled and encapsulated to achieve the desired effect on a long-term basis.

These approaches would eliminate the need for using multiple implants for the long-term, stable expression and delivery of more than one biologically active molecule to a single site.

This invention also contemplates using capsules containing cells that are genetically modified with a heterologous gene, which gene enables the cells to remain viable within the capsule upon implantation within a host mammal. In other words, the methods of this invention are also directed to methods of delivery of molecules within the implanted capsules.

In a specific embodiment of this invention we used the pNUT expression vector containing the human β-NGF gene operatively linked to the mouse metallothionein promoter to transfect BHK cells via the calcium phosphate co-precipitation method.

A variety of biocompatible immunoisolatory capsules are suitable for delivery of molecules according to this invention. Such capsules will allow for the passage of metabolites, nutrients and therapeutic substances while minimizing the detrimental effects of the host immune system. Preferably the capsule of this invention will be similar to those described in Aebischer et al., PCT publication WO 92/19195, incorporated herein by reference.

Most preferably the T1/2 membranes described herein are used to encapsulate the cells that are modified according to the methods of this invention. It will be appreciated that the T1/2 membranes described herein can also be used for encapsulation of any other suitable cell or cell lines. Thus, the T1/2 membranes of this invention can be used to encapsulate primary (non-dividing) cells, as well as dividing cells.

Useful biocompatible polymer capsules comprise (a) a core which contains a cell or cells, either suspended in a liquid medium or immobilized within a hydrogel or extracellular matrix, and (b) a surrounding or peripheral region of permselective matrix or membrane (jacket) which does not contain isolated cells, which is biocompatible, and which is sufficient to protect isolated cells if present in the core from detrimental immunological attack.

The core of the polymer capsule is constructed to provide a suitable local environment for the continued viability and function of the cells isolated therein.

Many transformed cells or cell lines are most advantageously isolated within a capsule having a liquid core. For example, cells can be isolated within a capsule whose core comprises a nutrient medium, optionally containing a liquid source of additional factors to sustain cell viability and function, such as fetal bovine or equine serum.

Microcapsules may sometimes be suitable for use in the methods and compositions of this invention. The fabrication of microcapsules have been described in Espevik et al., PCT publication WO 9107951, and Sefton, U.S. Pat. No. 4,353,888 incorporated herein by reference.

Suitably, the core may be composed of a matrix formed by a hydrogel which stabilizes the position of the cells in cell clumps. The term "hydrogel" herein refers to a three dimensional network of cross-linked hydrophilic polymers. The network is in the form of a gel, substantially composed of water, preferably but not limited to gels being greater than 90% water.

Compositions which form hydrogels fall into three classes. The first class carries a net negative charge (e.g., alginate). The second class carries a net positive charge (e.g., collagen and laminin). Examples of commercially available extracellular matrix components include Matrigel™ and Vitrogen™. Fibroblasts generally survive well in a positively charged matrix and are thus suitably enclosed in extracellular-matrix type hydrogels. The third class is net neutral in charge (e.g., highly crosslinked polyethylene oxide, or polyvinylalcohol). Any suitable matrix or spacer may be employed within the core, including precipitated chitosan, synthetic polymers and polymer blends, microcarriers and the like, depending upon the growth characteristics of the cells to be encapsulated.

Preferably, the capsules are immunoisolatory. To be immunoisolatory, the surrounding or peripheral region of the capsule should confer protection of the cells from the immune system of the host in whom the capsule is implanted, by preventing harmful substances of the host's body from entering the core of the vehicle, and by providing a physical barrier sufficient to prevent detrimental immunological contact between the isolated cells and the host's immune system. The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 75 microns are particularly preferred. Types of immunological attack which can be prevented or minimized by the use of the instant vehicle include attack by macrophages, neutrophils, cellular immune responses (e.g. natural killer cells and antibody-dependent T cell-mediated cytoloysis (ADCC), and humoral response (e.g., antibody-dependent complement mediated cytolysis).

Use of immunoisolatory capsules allows the implantation of xenogeneic cells or tissue, without a concomitant need to immunosuppress the recipient. Use of immunoisolatory capsules also allows use of unmatched cells (allografts). The type and vigor of an immune response to xenogeneic cells is expected to differ from the response encountered when syngeneic or allogeneic tissue is implanted into a recipient. This response may proceed primarily by cell-mediated, or by complement-mediated attack; the determining parameters in a particular case may be poorly understood. However, the exclusion of IgG from the core of the vehicle is not the touchstone of immunoprotection, because in most cases IgG alone is insufficient to produce cytolysis of the target cells or tissues. Using immunoisolatory macrocapsules, it is possible to deliver needed high molecular weight products or to provide metabolic functions pertaining to high molecular weight substances, provided that critical substances necessary to the mediation of immunological attack are excluded from the immunoisolatory capsule. These substances may comprise the complement attack complex component Clq, or they may comprise phagocytic or cytotoxic cells; the instant immunoisolatory capsule provides a protective barrier between these harmful substances and the isolated cells. Thus, an immunoisolatory capsule can be used for the delivery even from xenogeneic cells, products having a wide range of molecular sizes, such as insulin, parathyroid hormone, interleukin 3, erythropoietin, albumin, transferrin, enkephalins, endorphins, catecholamines, Factor VIII, NGF, BDNF, NT-3, NT-4/5, CNTF, GDNF, CDF/LIF, EGF, IGF, bFGF, aFGF, PDGF, TGF and the like.

Various polymers and polymer blends can be used to manufacture the capsule jacket, including polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, poly (acrylonitrile/covinyl chloride), as well as derivatives, copolymers and mixtures thereof.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient's blood vessels, are not preferred. Certain shapes, such as rectangles, patches, disks, cylinders, and flat sheets offer greater structural integrity and are preferable where retrieval is desired.

The instant capsule must provide, in at least one dimension, sufficiently close proximity of any isolated cells in the core to the surrounding tissues of the recipient, including the recipient's bloodstream, in order to maintain the viability and function of the isolated cells. However, the diffusional limitations of the materials used to form the capsule do not in all cases solely prescribe its configurational limits. Certain additives can be used which alter or enhance the diffusional properties, or nutrient or oxygen transport properties, of the basic vehicle. For example, the internal medium can be supplemented with oxygen-saturated perfluorocarbons, thus reducing the needs for immediate contact with blood-borne oxygen. This will allow isolated cells to remain viable while, for instance, a gradient of angiotensin is released from the capsule into the surrounding tissues, stimulating ingrowth of capillaries. References and methods for use of perfluorocarbons are given by Faithful, N. S. (1987) *Anaesthesia*, 42, pp. 234–242 and NASA Tech Briefs MSC-21480, U.S. Govt. Printing Office, Washington, D.C. 20402, incorporated herein by reference.

In one preferred embodiment, the implantable capsule is of a sufficient size and durability for complete retrieval after implantation. Such macrocapsules have a core of a preferable minimum volume of about 1 to 10 μl and depending upon use are easily fabricated to have a volume in excess of 100 μl.

The preferred capsule will have an inner single ultrafiltration membrane with a permselective pore-size permeability range of 60–98% BSA rejection coefficient and 50–90% ovalbumin rejection coefficient. The capsule may be in the form of a flat sheet sealed at the periphery or of a hollow fiber sealed at the ends as described in PCT application WO 92/19195. In a flat sheet format the two walls will be separated by a gap thickness of less than 1000 microns, preferably less than 300 microns. Wall thickness should be between about 25–200 microns, preferably between about 30–75 microns.

In a hollow fiber configuration, the fiber will have an inside diameter of less than 1500 microns, preferably less than 300–600 microns. In either geometry, the hydraulic permeability will be in the range of 1–100 mls/min/M$^2$/mmHg, preferably in the range of 25 to 70 mls/min/M$^2$/mmHg. The glucose mass transfer coefficient of the capsule, defined, measured and calculated as described by Dionne et al., *ASAIO Abstracts*, p. 99 (1993), and Colton et al., *The Kidney*, eds., Brenner BM and Rector FC, pp. 2425–89 (1981) will be greater than $10^{-6}$ cm/sec, preferably greater than $10^{-4}$ cm/sec.

The morphology of the outer wall surface of the capsule is variable. Previously described T1, T2, T4 membranes and the novel T1/2 membranes of this invention differ in their outer wall surface morphology. All these membranes are characterized by an inner permselective skin.

T1 membranes are characterized by an "open" or fenestrated non-permselective outer surface wall, and a trabecular wall structure between the outer and inner wall surfaces. See, e.g. Lacy et al., *Science*, 254, pp. 1782–84 (1991). The fenestrations of "macropores" in the outer wall surface of a T1 membrane typically occupy about 20%–40% of the total outer surface wall area. Typically, the macropores are 10 μm–15 μm in diameter or greater.

T2 membranes have a similar trabecular structure between the inner and outer walls but are characterized by a more "closed" or smoother outer surface wall. T2 membranes, typically are characterized by fewer than 10% macropores on the outer surface wall and virtually no macropores in the 5–15 μm diameter size range.

T4 membranes are further distinct in that the outer surface is also permselective, unlike the T1 or T2 membranes. T4 membranes are useful for CSF implantation sites, such as the ventricles or sub-arachnoid space, as well as other fluid bathed implantation sites.

For primate brain parenchyma, or other "solid" tissue implantation sites, we prefer to employ a smooth wall capsule which is substantially impermeable to cells. Others have described open walls which encourage microvascularization (see, e.g., Brauker et al., WO/92/07525). T1 and T1/2 capsules are especially suited for long term implants. We prefer T1/2 capsules.

T1/2 capsules are characterized by a total macropore distribution of between approximately 2–20%, preferably 2–15% of the total outer surface wall area. The macropores should fall within the size range of approximately 5 μm to about 15 μm in diameter. The relative distribution of pore sizes within this range can vary.

In one specific embodiment T1/2 hollow fiber membrane capsules made from PAN/PVC were utilized. According to this embodiment, the total macropore area was about 12% of the total outer wall surface area. Approximately 20% of the macropores ranged between 5–10 μm in diameter and about 80% of the macropores were about 10 μm in diameter.

In another specific embodiment, T1/2 hollow fiber membrane capsules were fabricated having a total macropore area of about 2.4% of the total outer wall surface area. Approximately 17% of the macropores were about 5 μm in diameter, about 33% were about 10 μm in diameter, and about 50% were about 15 μm in diameter.

In another specific embodiment, T1/2 hollow fiber membrane capsules were fabricated having a total macropore area of approximately 10% of the total outer wall surface area. Greater than 99% of these macropores ranged between 10–15 μm in diameter.

The quantification of outer surface macropore morphology can be accomplished using any standard method. We used two methods.

In one method, sections of the hollow fiber membrane are mounted for scanning electron microscopy. The outer surface of the fibers is then sputter coated with gold. Images of 1000X magnification are generated. One scanning electron micrograph at 1000X comprises an area of approximately 9.2 k μm$^2$ (115 μm×80 μm). On these images, a 10 μm diameter pore is 1 cm in diameter. Using a circle template, all pores can be classified as either 15 μm, 10 μm, 5 μm or 2.5 μm in diameter. The total percent of the outer surface wall open (i.e., as macropores) is calculated as (area occupied by all pores / total area of the micrograph)×100. Similarly calculations are used to determine the individual pore sizes.

Automated systems can be used to carry out the quantification. Scanning electron micrograph images at 1000X of hollow fiber membrane sections are prepared as described above. An image grabber is used to store the image for analysis (SCION Image). We used a Macintosh image processing and analysis program called NTH Image (Version 1.55) to process the stored images. This software was developed to perform morphometric analysis on histological samples and we have adapted it for hollow fiber morphometric analysis. Each pore is counted and a diameter is assigned. Calculations of total macropore area, and individual pore size are as described above.

The T1/2 fibers of this invention may be prepared by any suitable method known in the art. One method involves coextrusion of a polymeric casting solution and a coagulant through a coaxial spinneret by a suitable adjustment of luminal and casting solution flow rates using well known techniques described by Cabasso, I., *Encyclopedia of Chemical Technology*, 12, pp. 492–517 (1980). The coagulant which can include biological tissue fragments, organelles, or suspensions of cells and/or other therapeutic agents, as described in Dionne, WO 92/19195 and U.S. Pat. Nos. 5,158,881, 5,283,187 and 5,284,761, incorporated herein by reference.

According to those methods, T1 membranes may be formed by coextrusion of a polymer solution and coagulant solution through air before entering a quench bath. T2 membranes may be formed by coextruding the polymer, and coagulation solutions into humidified air or a mist and then into a bath. T4 membranes may be formed by coextrusion of the polymer and coagulant solutions directly into a coagulant bath, so that formation of the permselective membrane occurs on both outer and inner wall surfaces simultaneously.

T1/2 membranes may be formed using similar methods used to form T2 membranes. However, the mist or humidity at the coextrusion port may be controlled according to known methods to produced the desired outer surface morphology. Alternatively, the nozzle distance from a quench bath may be varied, according to routine methods. Further, if coextrusion is used to cast the membrane, the absolute and/or relative flow rates of polymer and coagulant may be adjusted to achieve the desired outer wall surface morphology. Finally, the polymer and coagulant solution compositions and temperatures can be varied to achieve the desired outer surface wall morphology. For example, the casting solution may be 10–15% PAN/PVC in DMSO (w/w) and the coagulant may be water, or other aqueous medium. Alternatively, the casting solution may be, e.g., 16% PAN/PVC, and the coagulant may be, e.g, 40% NMP, 60% $H_2O$ at 23° C.

Any suitable method of sealing the capsules may be used, including the employment of polymer adhesives and/or crimping, knotting and heat sealing. These sealing techniques are known in the art. In addition, any suitable "dry" sealing method can also be used. In such methods, a substantially non-porous fitting is provided through which the cell-containing solution is introduced. Subsequent to filling, the capsule is sealed. Such a method is described in copending U.S. application Ser. No. 08/082,407, herein incorporated by reference.

The methods and devices of this invention are intended for use in a mammalian host, recipient, subject or individual, preferably a primate, most preferably a human.

A number of different implantation sites are contemplated for the devices and methods of this invention. These implantation sites include the central nervous system, including the brain, spinal cord, and aqueous and vitreous humors of the eye. Preferred sites in the brain include the striatum, the cerebral cortex, subthalamic nuclei and nucleus Basalis of Maynert. Other preferred sites are the cerebrospinal fluid, most preferably the subarachnoid space and the lateral ventricles. This invention also contemplates implantation into the kidney subcapsular site, and intraperitoneal and subcutaneous sites, or any other therapeutically beneficial site.

In an embodiment of this invention, methods are provided for the treatment of diseases caused by neural degeneration. Examples of human diseases which are thought to be associated with neural degeneration include Alzheimer's disease, Huntington's disease, AIDS-related dementia, Amyotrophic Lateral Sclerosis (ALS) and Parkinson's disease.

Some animal models for neurodegenerative conditions are based on the premise that a specific insult may damage or kill neurons. In some cases this may even lead to a cascade of neuronal death which affects trophically interdependent neurons along pathways responsible for specific brain functions.

A strategy for treatment of neural degenerative conditions involves the localized administration of growth or trophic factors in order to (1) inhibit further damage to postsynaptic neurons, and (2) improve viability of cells subjected to the insult. Factors known to improve neuronal viability include NGF, BDNF, NT-3, NT-4/5, CNTF, GDNF, CDF/LIF, bFGF, aFGF, IGF, neurotensin, and Substance-P.

In one animal model for neurodegenerative excitotoxicity, the glutamate analog, quinolinic acid, is injected stereotaxically into the brain region known as the striatum and/or basal ganglia to produce neuropathology and symptoms analogous to those of patients suffering from Huntington's disease. Both the model and actual Huntington's disease are characterized by damage to neurons necessary for aspects of motor control. Furthermore, one of the early symptoms of Huntington's disease is loss of body weight (Sanberg, et al. *Med J Aust.*, 1, pp. 407–409 (1981)). Similar effects are also seen in the model system (Sanberg, et al. *Exp Neurol*, 66, pp. 444–466 (1979)). Quinolinic acid is also found at abnormally high levels in humans suffering from AIDS-related dementia.

Huntington's disease (HD) is an autosomal dominant disorder characterized by a progressive dementia coupled with bizarre uncontrollable movements and abnormal postures. HD is found in nearly all ethnic and racial groups with the prevalence rate in the U.S. approximately $5/1,000,000$ (Emerich, D. F. & Sanberg, *Neuromethods*, 21, pp. 65–134 (1992)). The manifestation of the disorder typically occurs in middle life, about 35–45 years of age, followed by an intractable course of mental deterioration and progressive motor abnormalities with death usually occurring within 15 years. Research into the neural pathology in HD has revealed a complex mosaic of related and interdependent neurochemical and histopathological alterations.

A variety of avenues have been explored to develop an animal model of HD. Recent investigations have centered on the relationship between striatal damage and the locomotor abnormalities resulting from the use of selective cytotoxic compounds. Glutamate is one of the major excitatory neurotransmitters found in the CNS. It can act, however, as a potent neurotoxin and a number of attempts have been made to develop animal models of HD based on the relatively specific cytotoxic effects of glutamate and other excitotoxic compounds. These compounds include structural analogs of glutamate, such as kainic acid (KA), ibotenic acid (IA), and the endogenous tryptophan metabolite quinolinic acid (QA). When injected into the brains of rats, in extremely small doses, these compounds produce a marked and locally restricted toxic effect while sparing axons of passage and afferent nerve terminals. The behavioral, neurochemical, and anatomical consequences of excitotoxicity resemble those observed in HD and have led to the speculation that an aberrant overproduction or breakdown of endogenous excitotoxic compounds is an etiological factor in HD.

Quinolinic acid, 2,3-pyridine dicarboxylic acid, a metabolite of tryptophan, has attracted a great deal of attention because of its powerful excitotoxic properties and wide distribution in both rat and human brain (Schwarcz and Kohler, *Neurosci. Lett.*, 38, pp. 85–90 (1983); and Schwarcz et al., *Science*, 219, pp. 316–318 (1983)). High concentrations of its catabolic enzyme, quinolinic acid phosphoribosyltransferase (QPRT), and immediate anabolic enzyme, 3-hydroxyanthranilic acid (3HAO), have been detected within the caudate suggesting that it normally serves a role in striatal functioning (Foster et al., *Brain Res.*, 336, pp. 207–214 (1985)). The striatum is among the structures most vulnerable to the excitotoxic effects of QA (Schwarcz and Kohler, (1983), Supra) and neonatal, but not mature, animals appear to be resistant to the toxic effects of QA corresponding roughly to the typical onset of HD in middle age.

Quinolinic acid has been reported to exert a more selective degenerative effect in the striatum than KA, which more closely resembles the pathology of HD (Beal, Synapse, 3, pp. 38–47 (1989); and Roberts and DiFiglia, *Synapse*, 3, pp. 363–371 (1989)). Like KA, QA injections cause depletions of GABAergic neurons while relatively sparing cholinergic neurons and axons of extrinsic origin. Unlike KA or IA, intrastriatal injections of QA appear to spare somatostatin- and neuropeptide Y-containing neurons suggesting that this model most closely reproduces the neuropathology observed in the disease (Beal et al., *J. Neuro Sci*, 8, pp. 3901–3908 (1988)).

According to the present invention, trophic factors are provided to the proper brain region by implanting a capsule containing cells, including genetically altered cells which secrete an appropriate factor. In some instances, the genetically altered cells are autologous to the host and may not require encapsulation.

Nerve growth factor-secreting cells such as BHK cells engineered to express human NGF represent a therapy for quinolinic acid induced neurodegeneration.

Another animal model involves lesion of the fimbria-fornix (rodents) or fornix (primates). In particular, neurons of the septohippocampal system are axotomized which leads to NGF-dependent degeneration and cell death in the septal cholinergic neurons. These lesions cause degenerative changes in brain areas similarly affected in Alzheimer's disease in humans.

According to the methods of this invention, NGF may be delivered to the affected area by the implantation of a capsule containing genetically altered cells which secrete NGF. Other neurotrophic factors such as CNTF, BDNF, bFGF, CDF/LIF may also protect similar or nonoverlapping populations of septal cholinergic neurons from atrophy and/or death. Preferably, the cells are fibroblasts which have been genetically engineered to produce recombinant human NGF.

Fornix lesions also cause behavioral deficits in the animal subjects of the model, most easily observed in tasks involving learning and memory. It has been reported that chronic administration of NGF to rats with fimbriafornix lesions accelerates the animals' behavioral recovery (Wills et al. Behav. Brain Res., 17, pp. 17–24 (1985)). In the present invention, implantation of the polymer capsule containing NGF-secreting cells provides a practical way to deliver NGF continuously to the appropriate brain region of the lesioned animal. The capsules of the present invention offer a practical form of therapy and/or prophylactic treatment for Alzheimer's victims whose conditions may be ameliorated by continuous delivery of NGF to specific brain regions.

The methods and compositions of this invention may be used for the treatment of age-related cognitive defects resulting from neural degeneration. Such treatment may augment cognitive performance, thus providing a symptomatic benefit. Alternatively, treatment may provide a neuroprotective effect, although not a symptomatic benefit. Age-related cognitive dysfunction and dementia in humans has been related to neuronal degeneration, especially of cholinergic basal forebrain neurons, and the decline of cortical and hippocampal levels of ChAT (Coyle et al., Science, 219, pp. 1184–90 (1983); Whitehouse et al., Science, 215, pp. 1237–39 (1982); Phelps et al., Neurobiol. Aging, 10, pp. 205–07 (1989); Gage et al., Neurobiol. Aging, 9, pp. 645–55 (1988)). Preclinical research attempting to produce a rodent model of dementia by selectively destroying cholinergic basal forebrain neurons has failed to produce large, lasting deficits in cognitive function. Aged rats exhibit neuropathology similar to that reported in aged and demented patients. The spatial-learning Morris water maze is extremely sensitive to the deleterious effects of these pathological processes (Morris, J. Neurosci. Meth., 11, pp. 47–60 (1984); Morris, Learning and Motivation, 12, pp. 239–60 (1981)). This task has been validated as a measure of age-related cognitive function—the performance of aged rats in this task is not strongly related to their motor, sensorimotor or visual deficits, factors which confound other tests of learning and memory (Gamzu, Ann. NY Acad. Sci., 444, pp. 370–93 (1985)).

As a cognitive task which requires the development of a spatial map (Eichenbaum et al., J. Neurosci., 10, pp. 3531–42 (1990)), the Morris water maze seems analogous to nonverbal tests of cognitive function that are especially sensitive to senescence and dementing disorders in the clinical setting. Therefore, this task seems to be valid for the assessment of potential new treatments for dementia. For example, several studies have reported that exogenous NGF improves Morris water maze performance in aged and learning-impaired rats. See, e.g., Fischer et al., Nature, 329, pp. 65–68 (1987); Fischer et al., J. Neurosci., 11, pp. 1889–1906 (1991).

Because NGF does not readily cross the blood brain barrier, its administration into the CNS requires the use of invasive procedures which compromise the integrity of the blood brain barrier. For example, in the rodent preclinical studies that demonstrated the potential efficacy of exogenous NGF, the NGF was administered with osmotic minipumps or through chronic intraventricular cannulae. Those techniques require repeated infusions into the brain, either through injections via the cannulae, or from pumps which must be replaced every time the reservoir is depleted. Every occasion in which the pump reservoir must be replaced or the injection syringe reinserted through the annulae represents another opportunity that contaminants might be introduced into the brain, which is especially susceptible to infection.

Even with the careful use of sterile procedures, there is risk of infection. It has been reported that even in intensive care units, intracerebroventricular catheters used to monitor intracranial pressure become infected with bacteria after about three days (Saffran, Perspectives in Biology and Medicine, 35, pp. 471–86 (1992). In addition to the risk of infection, there seems to be some risk associated with the infusion procedure. Infusions into the ventricles have been reported to produce hydrocephalus (Saffran et al., Brain Research, 492, pp. 245–254 (1989)) and continuous infusions of solutions into the parenchyma is associated with necrosis.

Use of fetal tissue is clouded by ethical concerns and unencapsulated non-fetal cells may be rejected or produce tumors. In addition, tissue taken from fetal sources may be highly variable. By encapsulating NGF-producing cells, exogenous NGF can be supplied with a relatively low risk of infection, without the use of fetal tissue, and without the risk of tissue rejection or tumor development.

Finally, concerns have also been expressed about whether exogenous NGF at the doses previously used itself might prove harmful or toxic, perhaps even accelerating the neurodegenerative processes associated with Alzheimer's disease (Saffran, Perspectives in Biology and Medicine, 35, pp. 471–86 (1992). It has been suggested that exogenous NGF might accelerate tangle formation, initiate axon sprouting of perivascular sympathetic axons potentially leading to changes in cerebral blood flow, or remodel the projections of basal forebrain neurons in response to the exogenous NGF such that not-yet-affected basal forebrain neurons become dysfunctional and thus accelerating the dementing process (Saffran, Perspectives in Biology and Medicine, 35, pp. 471–86 (1992)).

According to one aspect of this invention, the beneficial effects of exogenous NGF for the treatment of age related cognitive defects, including Huntington's disease, Parkinson's disease, Alzheimer's and ALS, may be obtained with doses much lower than previously reported to be effective for exogenous hNGF delivery.

Administration of the previously reported doses of NGF may have undesirable side effects including severe weight loss, pain, listlessness, hypophagia and recurrence of herpes infection.

According to this invention, capsular delivery of NGF, synthesized in vivo, to the brain ventricles, brain parenchyma, or other suitable CNS location, ranging from 1–1500 ng/day is desirable. The actual dosage of NGF, or other suitable factor, can be varied by implanting a fewer or greater number of capsules. We contemplate delivery of 1–1500, preferably 10–600, most preferably 50–500, ng NGF/human/day, for ventricular delivery and 1–1500, preferably 10–150, ng NGF/human/day for parenchymal delivery. These dosage ranges are significantly lower than those previously reported doses of NGF needed for CBF neuronal sparing/sprouting in rodent studies and in primate studies (17–350 µg/day), especially if the dosages are normalized to account for brain volume differences between rodents, primates and humans. Tuzynski et al., *J. Neurosci.*, 10, pp. 3604–14 (1990); Koliatsos et al., *Ann. Neurol.*, 30, pp. 831–840 (1991); Kekker *Experimental Neurol.*, 112, pp. 161–73 (1991); Dekker et al., *Neuroscience*, 60, pp. 299–309 (1994). In the one clinical patient evaluated, the dose of NGF delivered was 75 µg/day. (Olson et al., *J. Neural Trans.*, 4, pp. 79–95 (1992)). In one embodiment, genetically-modified cells secreting human NGF (hNGF) are encapsulated in semipermeable membranes, and implanted intraventricularly or intraparenchymally in a suitable mammalian host, preferably a primate, most preferably a human.

U.S. Pat. Nos. 5,106,627 and 5,156,844, incorporated herein by reference, refer to solid polymer inserts or encapsulated cells that produce a growth factor in close proximity to encapsulated neurotransmitter secreting cells.

In another embodiment, encapsulated cells that secrete a growth factor (e.g., including NGF, BDNF, platelet derived factor "PDGF", fibroblast growth factor "FGF", epidermal growth factor "EGF", NT-3, NT-4/5, CNTF, gDNF) may be used enhance the survival and growth of unencapsulated cell grafts.

The growth factor may be specific for the unencapsulated cell type, or may have a general effect. A particular embodiment contemplates co-implantation of encapsulated growth factor secreting cells with unencapsulated neurotransmitter or analgesic (e.g., enkephalins, endorphins or catecholamines) secreting cells into the central nervous system, in particular the lateral ventricles or striatum. We prefer co-implanting encapsulated NGF-secreting cells (as described herein) with unencapsulated adrenal chromaffin cells.

One of skill in the art will appreciate that effect of the encapsulated growth factor secreting cells on the unencapsulated cells may vary according to the implant location. We prefer intrastriatal implants.

In order that this invention may be better understood, the following examples are set forth. These examples are for purposes of illustration only, and are not to be construed as limiting the scope of this invention in any manner.

EXAMPLES

EXAMPLE 1: Encapsulated NGF-Secreting BHK Cells Implanted In The CNS of Adult Rats Human β-NGF expression and BHK cell line production The human gene for β-NGF coding for the complete amino acid sequence of the pre-pro form of NGF was subcloned behind the mouse metallothionein promoter in an expression construct that contains the mutant form of dihydrofolate reductase (see, e.g., Kaufman U.S. Pat. No. 4,470, 461) driven by the SV40 promoter (FIG. 1).

Two human genomic clones coding for the 5' and 3' ends of the β-NGF gene were purchased from ATCC (phbeta N8D8, phbeta N8B9). A 440 bp 5' ScaI-RcoRl fragment from phbeta N8D8 was ligated to a 3' 2.0 kb RcoRl fragment isolated from phbeta N8B9. The spliced NGF genomic sequence contained ~37 bp of the 3' end of the first intron, the double ATG sequence believed to be the protein translation start for pre-pro-NGF and the complete coding sequence and entire 3' untranslated region of the human gene (Hoyle et al., *Neuron* 10, pp. 1019–1034 (1993)). The combined 2.51 kb β-NGF construct was subcloned into the DHFR based pNUT expression vector (Baetge et al., *Proc. Natl. Acad. Sci. USA*, 83, pp. 5454–5458 (1986)) immediately downstream from the mouse metallothionein-I promoter (−650 to +7) and the first intron of the rat insulin II gens (Palmiter R. D. et al., *Proc. Natl. Acad. Sci. USA*, 88, pp. 478–482 (1991)). The pNUT-β-NGF construct (see FIG. 1) was introduced into BHK cells using a standard calcium phosphate-mediated transfection method. Transfected BHK cells were selected in medium containing 200 µM methotrexate (Sigma) for 3–4 weeks and resistant cells were maintained as a polyclonal population either with or without 200 µM methotrexate.

Quantitation of NGF bioactivity

Nerve growth factor (NGF) causes a marked outgrowth of neurite processes in PC12 cells and as such provides a rapid and sensitive assay for NGF bioactivity. To test for the bioactivity of the NGF produced by the NGF-transfected BHK cells, conditioned medium (CM) from parental BHK cells (BHK-control) and BHK-NGF cells were added to the PC12A (Schweitzer and Kelly, *J. Cell Biol.*, 101, pp. 667–676 (1985)) cells grown on 6 well standard tissue culture plates. As a control, 25 S mouse NGF was added to some of the wells to induce neurites (50 ng/ml). The PC12A cells were scored for neurites that were ≧3 times the length of the cell body diameter over a period of 1–4 days. NGF bioassays were also performed upon retrieval of implanted control and NGF-secreting, BHK cell-loaded, capsules by adding CM from the capsules to naive PC12A cells taken from capsules incubated with fresh medium for 24 hours. In all of the experiments, CM from BHK-NGF cells produced a robust neurite outgrowth in PC12A cells within 24 hours indicating that the NGF produced from the BHK cells was bioactive. BHK-controls showed no such capacity to elicit neurite outgrowth in the PC12A cells in parallel experiments.

To determine whether the neurite outgrowth was due to factors other than NGF, such as bFGF, we added an NGF blocking antibody (mouse anti-β-NGF; Boehringer-Mannheim Cat. #1008-220) in combination with CM and recombinant hNGF. The addition of this blocking antibody fully inhibited neurite outgrowth from the PC12A cells in a dose-dependent fashion. Finally, we performed a set of experiments probing the BHK-control cell conditioned medium by ELISA for the presence of basic fibroblast growth factor (bFGF). Using a bFGF ELISA (Research and Diagnostics Systems, Quantikine™, human FGF basic ELISA kit; Burgess et al. *Ann. Rev. Biochem*, 58, p. 575 (1989)), we were unable to detect any bFGF in heavily conditioned medium from the BHK cells. Both of these experiments clearly indicate that the neurite outgrowth seen in the PC12A cells in response to BHK-NGF CM is due to the presence of secreted NGF.

NGF ELISA

The quantitation of NGF expression from the encapsulated and the unencapsulated BHK-NGF cells was performed as follows: All of the reagents were obtained from Boehringer Mannheim Biochemicals unless otherwise noted. Nunc-Immuno MaxiSorp ELISA plates were coated with 150 μl per well of anti-mouse-β(2.5S) nerve growth factor at 1 ng/ml in coating buffer (1×PBS without CACl$_2$ and without MgCl$_2$/0.2% sodium azide; pH 9.6). The coated plates were incubated at 37° C. for at least 2 hours or alternatively at 4° C. overnight. The coating solution was withdrawn from the wells and the wells were washed three times with 300 μl wash buffer (50 mMTris-HCl/200 mM NaCl/10 mM CaCl$_2$/0.1% Triton X-100/0.1% sodium azide; pH 7.0). The wells were then blocked with 300 μl of coating solution with 10 mg/ml of bovine serum albumin (BSA) at room temperature for at least 30 minutes. The wells were then washed three times with 300 μl wash buffer. Conditioned medium samples were diluted 1:1 in 2×sample buffer (the sample buffer is the same as wash buffer, only with 2% BSA). 100 μl of the prepared samples were loaded into the wells. The plates were covered and then incubated for at least 2 hours at 37° C. or overnight at 4° C. The solutions were removed from the wells by suction and washed three times with 300 μl of wash buffer. To each well, 100 μl of 4U/ml of anti-mouse-β(2.5S) nerve growth factor-β-gal conjugate was added. The plates were incubated at 37° C. for at least 1 hour. The solutions were removed from the wells by suction and washed three times with 300 μl of wash buffer. Finally, 200 μl of chlorophenol red-β-D-galactopyranoside substrate solution (40 mg CPRG in 100 mM Hepes/150 mM NaCl/2 mM MgCl$_2$/0.1% sodium azide/1% BSA; pH 7.0) was added to the wells and incubated at 37° C. After approximately 30 minutes to one hour or after the color development was sufficient for photometric determination at 570 nm, the samples were analyzed on a plate reader and measured against recombinant NGF protein standards.

c-fos induction assay

Qualitative c-fos induction elicited by NGF administration to PC12A cells was measured by an immunofluorescence assay. PC12A cells were plated at a density of 100,000 cells per ml on poly ornithine-treated glass coverslips (12 mm) and allowed to equilibrate for at least 24 hours in a 24-well plate. Cells were grown in the same medium as previously described in the section on neurite outgrowth bioassay.

To test for c-fos induction in the PC12A cells, conditioned medium from capsules containing BHK and BHK-NGF cells or recombinant human NGF (50 ng/ml) was added to the PC12A cells for 2 hours and allowed to incubate at 37° C. and 5% CO$_2$. Following this incubation, the coverslips were fixed with 4% paraformaldehyde (in 0.1M PBS, pH 7.4), washed 2X with 10 mM glycine in PBS, permeabilized with 1% triton X100 (in PBS for 10 minutes) and 1% nonidet P40 (in PBS for 10 minutes). The cells on coverslips were washed 3×5 minutes with PBS, blocked with 5% normal goat serum (NGS) in PBS for 1 hour and incubated in a rabbit polyclonal antiserum (Oncogene Science) raised against c-fos diluted 1:10 in 1% NGS in PBS for 3 hours. The coverslips were then washed 2×5 minutes with PBS and incubated with a fluoresce-inconjugated goat anti-rabbit IgG antibody. Finally, the coverslips were washed 2X with PBS and mounted with Citifluor® antifadent and viewed by fluorescence microscopy. Fluorescence was monitored by microscopy and c-fos induction measured by the presence of fluorescently labeled nuclei.

Encapsulation procedure

Asymmetric single skin hollow fibers were cast from solutions of 12.5% poly (acrylonitrile vinyl chloride, i.e. PAN-PVC) copolymer in dimethyl sulfoxide (w/w). The fabrication process is known as phase inversion using a dry-wet (jet) spinning technique according to Cabasso, *Encyclopedia of Chemical Technology*, 12, pp. 492–517 (1980). After the spinning process, the hollow fibers were sterilely transferred into a distilled water bath containing 25% glycerol, which provides a method for keeping the pores intact during the drying procedure (Cabasso, 1980, supra). The fibers produced (XP 11) were a T1/2 membrane type, having an inner diameter of 450±25 μm, a hydraulic permeability of 53 ml/(m$^2$ min mmHg), a BSA rejection coefficient of 88.7±2.1%, an ovalbumin rejection coefficient of 82.0±1.7%, and a glucose mass transfer coefficient of about 8×10$^{-4}$ cm/s. After drying, devices were fabricated by mounting a length of 6–7 mm dry hollow fiber, with a distal seal, onto a light-cured acrylate hub with a septal fixture at the proximal end which has loading access for cells to be injected into the lumen of the device. Glycerol was removed from the devices with 70% filter sterilized ethanol and placed in HBSS prior to the encapsulation procedure.

Cells were loaded into the prefabricated encapsulation devices as follows: either BHK-control cells or BHK-NGF cells were loaded into prefabricated devices at a density of approximately 10$^7$/ml. The BHK cell suspensions at a density of 2×10$^7$/ml were mixed 1:1 with physiologic Vitrogen® (Celtrix, Palo Alto, CA), and infused into the prefabricated devices through the septal access port. After infusing 2–2.5 μl of the cellular suspension, the septum was cracked off and the access port was sealed using a light-cured acrylate (Zeneca). BHK cell-loaded devices were maintained in a serum-free defined medium, PC1 (Hycor), for 4–5 days prior to implantation. After 3 or 4 days in vitro, the cell-loaded capsules were washed twice in HBSS, and placed in 1 ml of fresh medium to be analyzed for NGF by ELISA.

Long Term β-NGF Expression in Adult Rat CNS

Our in vitro experiments demonstrated long-term, stable, high level expression of human β-NGF in BHK cells. To determine if this long-term, stable expression could be achieved in vivo, we implanted capsules containing BHK cells into the CNS of adult Lewis rats.

Prior to implantation, conditioned medium (CM) taken from BHK-NGF and BHK-control capsules were subjected to neurite outgrowth assay for NGF as described above. 0.5 ml of CM from the BHK-NGF cells was equivalent to 50 ng/ml of exogenously added NGF, in terms of the extens of neurite outgrowth, whereas CM from the BHK-control cells did not contain detectable levels of NGF.

The capsules were implanted into the striatum of adult Lewis rats for one, three and six month periods. Upon explanation, the capsules were tested for NGF production by the neurite outgrowth assay.

After 1, 3, and 6 months in vivo, the BHK-NGF loaded capsules were able to produce neurite outgrowth in PC12A cells equivalent to or greater than 50 ng/ml of NGF. No NGF activity was detectable in the CM from the BHK-control capsules. As shown in Table I, ELISA quantitation of the samples from the encapsulated BHK-NGF cells release up to about 20 ng/24 hr/capsule after 3 and 6 months in vivo.

TABLE I

| NGF AS MEASURED BY ELISA IN ng/CAPSULE/24 HR | | |
|---|---|---|
| Condition | Pre- | Post- |
| 3 mo. nv1 (BHK-NGF) | NA | 17.1 |
| 3 mo. nv2 (BHK-NGF) | NA | 13.1 |
| 3 mo. nv3 (BHK-CONTROL) | NA | 0.1 |

TABLE I-continued

| NGF AS MEASURED BY ELISA IN ng/CAPSULE/24 HR | | |
|---|---|---|
| Condition | Pre- | Post- |
| 6 mo. nv1 (BHK-NGF) | NA | 21.6 |
| 6 mo. nv2 (BHK-NGF) | NA | 2.8 |
| 6 mo. nv3 (BHK-CONTROL) | NA | 0.1 |

NA = Not Available; no medium samples for NGF ELISA pre-implant nv1, nv2 and nv3 represent naive animals EXAMPLE 2: Fimbria-Fornix Lesion Study in Rats To evaluate the ability of encapsulated NGF-secreting BHK cells (as described in Example 1) to release efficacious amounts of NGF in vivo, fimbria-fornix aspirative lesions were stereotaxically performed in 14 Lewis rats. Immediately after lesioning, a BHK-control or BHK-NGF loaded XP-11 device, as described in Example 1, was stereotaxically implanted into the lesion site.

Subjects

Adult male Lewis rats (Harlan Breeders, Indianapolis, IN) approximately 3 months old and weighing approximately 300 grams were used in the following studies. The animals were housed in groups of three in a temperature and humidity controlled colony room which was maintained on a 12 hour light/dark cycle with lights on at 0700 hours.

Stereotaxic surgery

Immediately prior to surgery, rats were anesthetized with an intramuscular injection of a ketamine, xylazine and acepromazine mixture and positioned in a Kopf stereotoxic instrument (see Emerich et al. 1992). A sagittal incision was made in the scalp and a craniotomy performed extending 2.0 mm posterior and 3.0 mm lateral from Bregma. An aspirative device with a 20 gauge tip was mounted to a stereotaxic frame (Kopf Instruments) and the medial parietal cortex, cingulate cortex, corpus callosum, dorsal hippocampus, dorsal thalamus and fimbria-fornix were aspirated by placing the suction tip 1.40 mm posterior to Bregma and lowering it immediately lateral to the sagittal sinus to a depth of 5.0 mm. The tip was then moved laterally in 0.5 mm increments until a position of 3.0 mm lateral to Bregma was attained. Immediately following the aspiration, the rats were unilaterally implanted with either transfected (N=8) or non-transfected BHK cell-containing capsules (N=6) by placing the capsule within an 18 gauge Teflon catheter mounted to the stereotaxic frame. Each device measured 0.7 cm in length by 600 microns in diameter and contained approximately 15-25×10$^3$ cells.

A stainless steel obdurator was placed within the cannula, and the obdurator held in place while the outer cannula was raised to passively place the capsule within the previously prepared cavity. The stereotaxic coordinates for implantation were: 0.5 mm posterior to Bregma, 1.0 mm lateral to the sagittal suture and 7.5 mm below the cortical surface.

Histology

Animals were anesthetized 3 weeks following surgery and prepared for histological analysis. Animals were transcardially perfused, using a peristaltic pump, with the following: 20 ml saline (0.9%, room temperature), 120 ml of glutaraldehyde (0.1%), 500 ml 0.1% glutaraldehyde/4% paraformaldehyde, 300 ml of paraformaldehyde (4%), and finally 300 ml of 10% sucrose. All solutions were ice cold (4° C.) and prepared in phosphate buffered saline (pH=7.4) unless otherwise noted.

Brains were removed following fixation, placed in 25% buffered sucrose (pH=7.4) and refrigerated for 24–48 hours. Tissue was cut at 20 μm intervals on a cryostat and mounted onto polylysine coated slides. Every 3rd section throughout the septum was saved and processed for choline acetyltransferase (CHAT) immunoreactivity according to the following protocol: (1) overnight incubation in PBS containing 0.8% Triton X-100+10% normal serum, (2) 48 hour incubation with primary antibody (goat antiserum to CHAT; Chemicon) at a dilution of 1:1000, (3) 6×5 minute rinses in PBS+0.2% Triton X-100 followed by a 1.5 hour incubation in biotinylated secondary antibody (IgG), (4) 6×5 minute rinses in PBS+0.2% Triton X-100, (5) incubation with Avidin-Biotin Complex (ABC, Vector elite) for 1.5 hours, (6) 3×5 minutes rinses in PBS, (7) 5 minute rinse in distilled water, (8) incubation with 3,3-diaminobenzidine (DAB) (0.05%)+2% nickel ammonium sulfate dissolved in 0.1% Tris buffer for 5 minutes followed by hydrogen peroxide (0.01%) for 5 minutes, (9) the reaction was terminated by 3×1 minute rinses in PBS.

Sections were mounted, dehydrated and coverslipped. Adjacent sections were stained for hematoxylin and eosin (H+E). To verify the extent of lesion produced following aspirations of the fimbria-fornix, every 10th section was taken throughout the hippocampus and stained for acetylcholinesterase according to the method of Van Ootegan et al. (*Brain Res. Bull.*, 12, pp. 543–553 (1984)). For quantification of cholinergic cell loss, ChAT-positive neurons were counted in the medial septum and vertical limb of the diagonal band at a magnification of 10X. Representative sections (3 per brain) located approximately 0.7, 0.5 and 0.2 mm anterior to Bregma from each animal were used for this analysis.

NGF Release Results

At 3½ weeks post implantation the animals were anesthetized and the devices retrieved by gently pulling the silicone tethers. Each capsule was incubated for 24 hours in 1 ml of medium and CM was assayed for NGF by ELISA. Pre- and post- transplantation NGF secretion levels are listed in Table II.

TABLE II

| NGF AS MEASURED BY ELISA IN ng/CAPSULE/24 HR | | | | |
|---|---|---|---|---|
| Condition | Pre- | ± SD | Post- | ± SD |
| F/F UNILAT (n = 4) | 27.2 | 2.5 | 5.2 | 0.9 |
| CONTROLS (n = 6) | 0.1 | 0.05 | 0.15 | 0.1 |

Histological sections taken through the hippocampus and septum of all animals were examined by immunocytochemistry for acetylcholinesterase (AchE) in the hippocampus and choline acetyltransferase (CHAT) in the septum. AchE immunoreactivity in the hippocampus was used as a second indicator of lesion completeness and CHAT-immunoreactivity in the septum provided evidence for cholinergic cell body sparing or atrophy as a result of transplant and lesions. A representative comparison of AchE immunostaining in the hippocampus of the lesioned-vs-control side demonstrated nearly complete loss of AchE afferents to the lesioned side.

Figure 2:
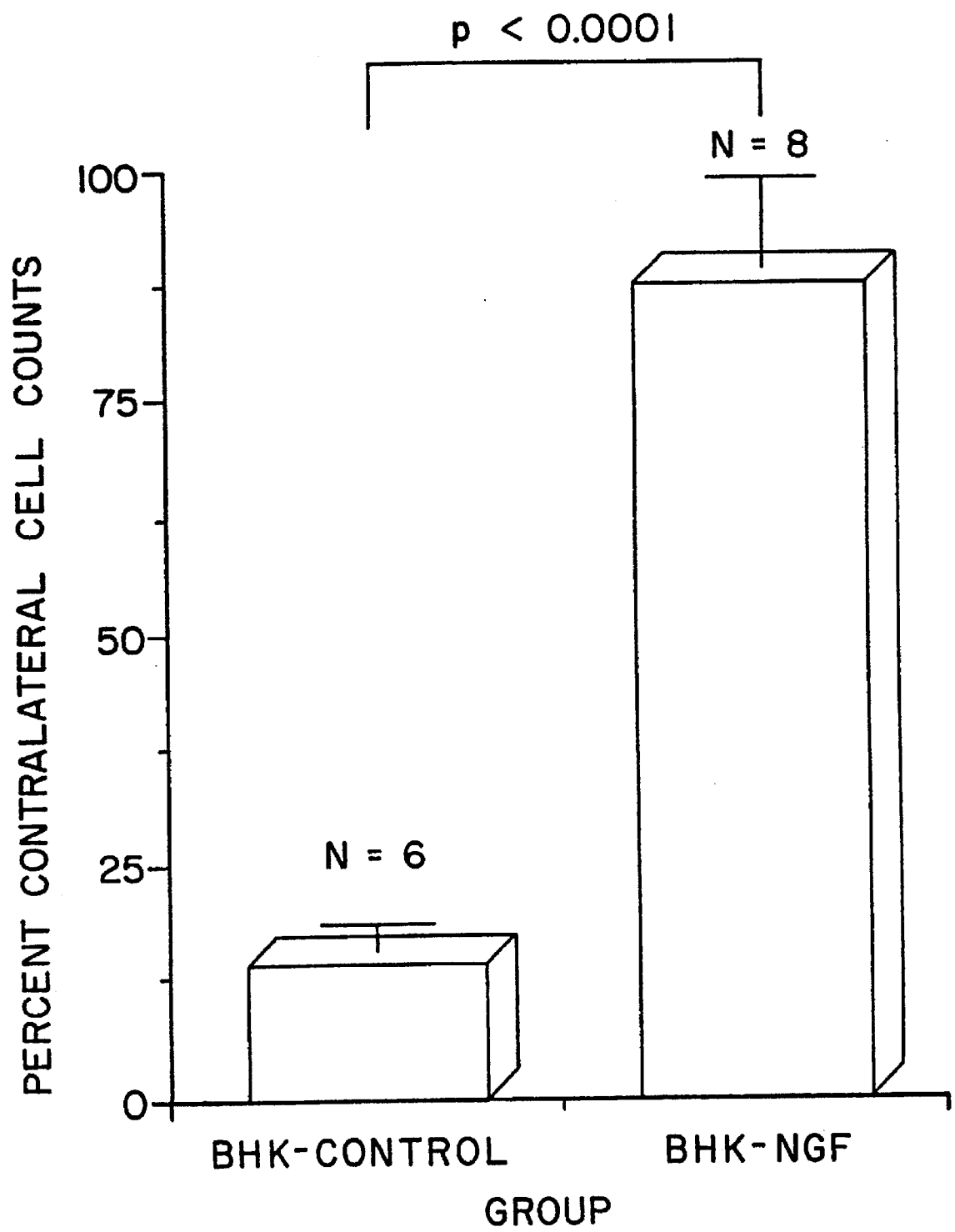
FIG. 2 depicts the percentage of septal cholinergic neurons surviving after fimbria-fornix transection lesion with and without NGF secreting BHK cell implants.

Total CHAT-positive neurons remaining in the septum 3½ weeks post-lesion in BHK-control and BHK-NGF implanted animals were counted and the combined results are shown in FIG. 2. Quantitation of ChAT-positive neurons revealed that with BHK-control capsules, only 15±3% of the neurons remained positive on the lesioned side of the brain compared with the non-lesioned side, whereas with the BHK-NGF capsules, 90±5% of the cholineric neurons were immunopositive for CHAT. Encapsulated Cell survival was equivalent between the BHK-control and BHK-hNGF cell-loaded capsules (data not shown).

EXAMPLE 3: primate Fornix Lesion

Example 2 demonstrated that the chronic delivery of hNGF from the BHK cells of this invention into the lateral ventricle of adult rats with fimbria-fornix lesions protects the medial septal cholinergic neurons that otherwise would have died as a result of the lesion. Similar experiments are described here performed in nonhuman primates. Lesioning of the fornix in monkeys (Cebus apella) is described in (Kordower and Fiandaca, J. Comp. Neurol., 298, pp. 443, (1990)).

Adult cynomolgous monkeys were used in these lesion experiments. After the unilateral lesion was complete, 5 XP-11 capsule devices, as described in Example 1, (identified by number) were manually placed within the lateral ventricle adjacent to the medial septum, ipsilateral to the lesion. As controls, some animals were implanted with devices loaded with BHK-control cells. Following the implantation procedure, the surgical sites were closed and the animal were allowed to recover and were closely monitored for 3½ weeks. Following the 3½ week survival period, the numbered capsules were carefully removed and placed in standard cell culture medium and then reassayed by ELISA for NGF release as they were pre-implantation (Table III). The animals were then sacrificed by perfusing with aldehyde fixatives and the brains were sectioned and processed for histochemical and immunohistochemical procedures.

TABLE III

± NGF INTO F ASPIRATIVE LESIONED PRIMATES AS MEASURED BY ELISA IN ng/CAPSULE/24 HR

| Animal No. | Pre- | ±SD | Post- | ±SD |
|---|---|---|---|---|
| B 105 (BHK-NGF) (n = 5) | 24.9 | 9.4 | 14.1 | 4.6 |
| B 106 (BHK-NGF) (n = 5) | 29.6 | 8.6 | 9.2 | 0.8 |
| B 108 (BHK-CONTROL) (n = 5) | 0.6 | 1.2 | 0.2 | 0.2 |

The data shown in Table III represents analysis of two BHK-NGF implanted monkeys and one control monkey. Subsequent analysis of NGF release data from an additional 6 animals in the same study revealed that the average level of hNGF produced by the capsules within prior to implantation was 21.4+2.0 ng/capsule/24 hours and 8.5+1.2 ng/capsule/24 hours in the retrieved capsules as measured by the NGF ELISA. Because each monkey was implanted with five capsules, the total amount of NGF produced per animal was 107 ng/24 hours and 41.5 ng/24 hours prior to implant and 1 month following implant, respectively. The BHK-control capsules produced no detectable hNGF (assay sensitive to 25 pg NGF/ml).

Animals rapidly recovered from surgery and survived the duration of the experiment. Animals receiving BHK-hNGF-containing capsules were lethargic and exhibited decreased appetite for several days following surgery. One of these animals also exhibited multiple seizures beginning approximately 2 days following surgery and dissipating within 5 days following surgery. No such complications were noted in any of the animals receiving BHK-control cell implants, and no differences were observed between the BHK-hNGF and BHK-control animals after the first postsurgical week.

The polymer capsules were left in situ from one animal receiving BHK-control implants. In all other monkeys, the BHK cell-loaded devices were retrieved from the lateral ventricles 23–28 days following implantation with little to no host tissue adhering to the capsules.

Based on visual inspection at the time of capsule removal, all capsules were located within the lateral ventricle and abutted both the head of the caudate and the lateral septum. All capsules were removed intact, and there was no evidence that any capsule broke either in situ or during the retrieval procedure. The cell-loaded devices were left in situ in 1 BHK-control animal to demonstrate placement of the devices and assess the host tissue response. The host response to the capsules in this animal and all others was minimal. There was a relative paucity of reactive glia, which, if observed at all, was only seen at circumscribed locations at the graft-host interface. Furthermore, other non-neuronal cells such as macrophages were not observed within the perigraft region.

All monkeys displayed complete transections of the fornix as revealed by a comprehensive loss of acetylcholinesterase-containing fibers within the hippocampus ipsilateral to the lesion. Control monkeys that were either unimplanted or received BHK-control (non-NGF secreting) cell implants did not differ from each other and displayed extensive losses of choline acetyltransferase and p75 NGF receptor (NGFr)-immunoreactive neurons within the medical septum (MS; 53 and 54% respectively) and vertical limb of the diagonal band (VLDB; 21 and 30%, respectively) ipsilateral to the lesion. In contrast, monkeys receiving implants of BHK-hNGF cells exhibited a only a modest loss of cholinergic neurons within the septum (19 and 20%, respectively) and VLDB (7%). Furthermore, only implants of hNGF-secreting cells induced a dense sprouting of cholinergic fibers within the septum, which ramified against the ependymal lining of the ventricle adjacent to the transplant site. Examination of the retrieved capsules revealed an abundance of cells that produced detectable levels of hNGF in a sufficient concentration to differentiate PC12A cells in culture.

EXAMPLE 4: Effects of BHK-NGF Implants in Animal Models for Huntington's Disease

A. RODENTS

Surgery and transplantation

Immediately prior to surgery, Lewis rats were anesthetized with sodium pentobarbital (45 mg/kg, i.p.), and positioned in a Kopf stereotaxic instrument. A sagittal incision was made in the scalp and two holes drilled for the placement of XP-11 polymer capsules containing NGF-secreting BHK cells (as described in Example 1) into the lateral ventricle. Rats were either uni- or bilaterally implanted by placing the capsule within an 18 gauge Teflon catheter mounted to the stereotaxis frame and lowering it to the appropriate site. The stereotaxic coordinates for implantation were: 0.5 mm anterior to Bregma, 1.5 mm lateral to the sagittal suture and 8.0 mm below the cortical surface.

Approximately one week later, animals were anesthetized, placed in a stereotaxic instrument and injected unilaterally with 225 (unilateral) or 150 nmol (bilateral) of QA or the phosphate-buffered saline vehicle into the striatum at the following coordinates: AP=1.2 mm, ML=±2.6 mm and DV=5.5 mm ventral from the surface of the brain. QA was dissolved in 2N sodium hydroxide and diluted with phosphate buffer at pH 7.2 to a final pH of 7.4 and concentration of 225 nmol/ul. QA was infused into each striatum, using a 28-gauge Hamilton syringe, over five minutes in a volume of 1 μl. The injection cannula was left in place for an additional two minutes to allow for diffusion of the perfusate. This procedure resulted in the formation of three experimental groups: 1) quinolinic acid only (QA), quinolinic acid+NGF-secreting BHK cells (QA/NGF), and quinolinic acid+non-NGF-secreting BHK cells (QA/NON-NGF). Immediately following surgery, animals were injected i.p. with 10 ml of lactated Ringer's solution. Animals were housed postoperatively with food mash and water available ad lib.

Behavioral testing

Rotational behavior:

Beginning 10 days following unilateral quinolinic acid injections, animals were tested for apomorphine-induced rotation behavior in automated rotometers (Rotoscan, Omnitech Instruments) which were connected to an IBM computer for automated data collection. Animals were placed into the test chamber for a 5 minute habituation period, were then injected with apomorphine (1.0 mg/kg in normal saline containing 0.1% ascorbate) and tested for an additional 30 minutes. Sensitization of apomorphine-induced rotation behavior occurs following excitotoxin lesions of the striatum. Therefore, animals were tested 4 times with each session separated by a 3–4 day interval. Rotations were defined as complete 360 degree ipsilateral turns and were reported as the net difference between the two directions.

Spontaneous locomotor activity:

Prior to surgery and 30 days following bilateral QA each animal was placed individually into one of five open-field boxes (40×40×35 cm) in an automated Digiscan-16 Animal Activity Monitor System (Omnitech Electronics, Columbus, OH) and tested for locomotor activity during a 1 hour test period. The following locomotor variables were collected: (1) horizontal activity (HA): the total number of interruptions of the horizontal sensors; (2) total distance (TD): the distance travelled by the animal in inches; (3) number of movements (NM): this parameter increased by one each time a movement was registered by the breaking of a beam separated by at least one second from the last interruption; (4) movement time (MT): the time in seconds that the animal spent in motion; (5) average speed (AS): the average speed of the animal's movement in cm/second; (6) average distance (AD): the average distance the animal moved in inches during a movement bout; (7) vertical activity (VA): the total number of beam interruptions in the vertical sensors; (8) vertical time (VT): this parameter increased while an animal was breaking the beam of a vertical sensor; (9) number of vertical movements (VM): this increased with vertical sensor-beam interruptions that were separated by at least one (1) second; (10) number of stereotypic movements (NS): this parameter increased when the same beams were broken repeatedly with one second in between; (11) stereotypy time (SC): the accumulated time spent in stereotypy.

Catalepsy:

One day following locomotor activity testing, animals were tested for hypokinesia (catalepsy) following administration of the D1 and D2 dopamine receptor antagonists haloperidol and SCH2388. Catalepsy was measured using the bar test in which the rear feet of the animals were placed on a platform and their front feet were placed on a horizontal bar (0.6 cm in diameter) suspended 9.0 cm above the platform. The degree of catalepsy produced in the animals was measured by how long it took for each animal to remove itself from the bar. A maximum of 300 seconds was allowed. Animals were randomly assigned to one of three treatment groups and injected with either haloperidol (1.0 mg/kg), SCH23388 (1.0 mg/kg) or control vehicle (0.9% saline). Bar tests were conducted again at 1, 2, 3 and 4 hours after administration of drug and/or control vehicle. All animals were tested under each treatment condition with tests separated by a 3–4 day interval.

Results

Figure 3:
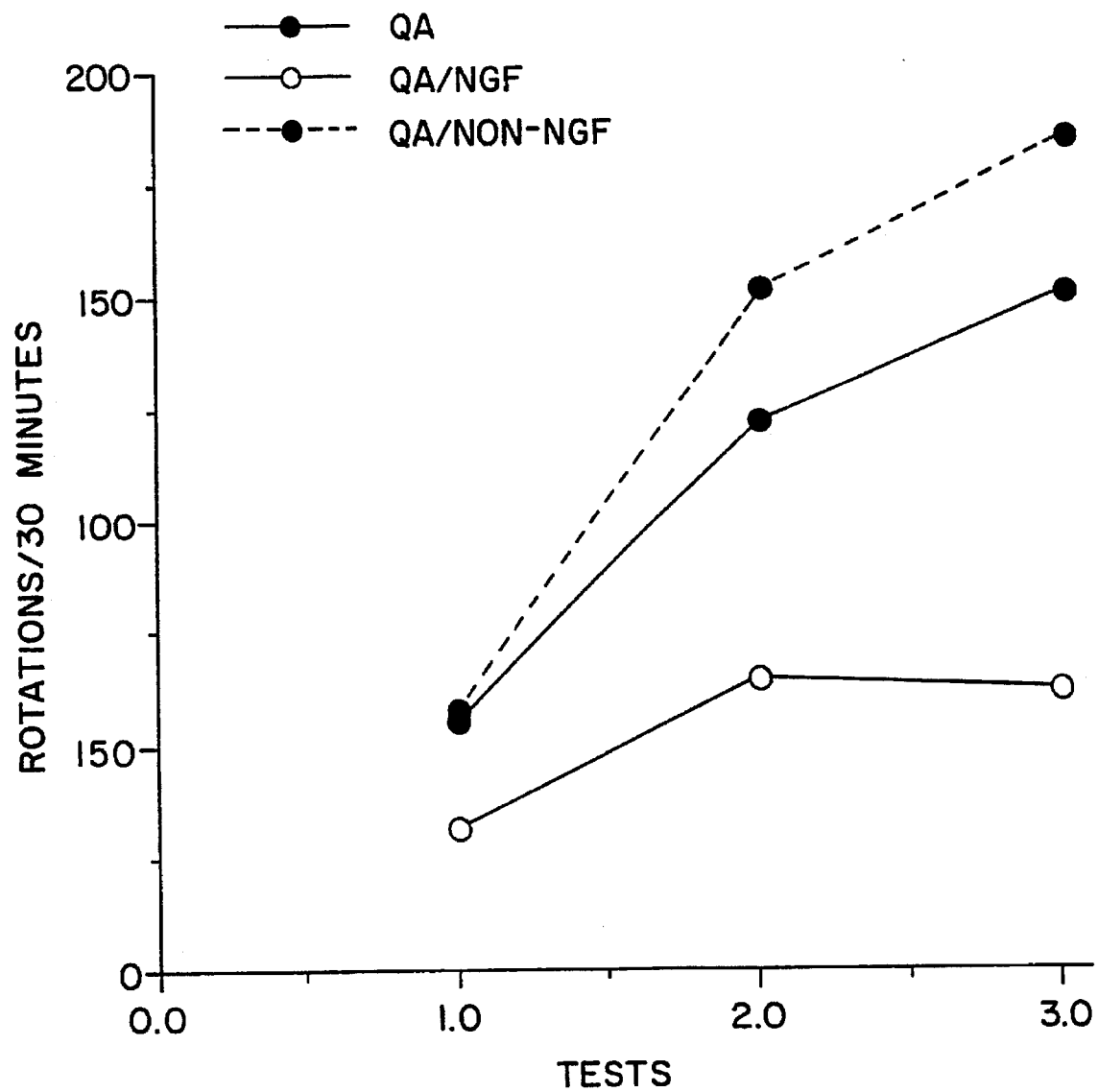
FIG. 3 depicts the effects of encapsulated NGF-secreting BHK cells on apomorphine-induced rotations in unilaterally lesioned QA rats. Animals were tested for rotation behavior on three separate occasions. Data are presented as the mean (±) SEM number of complete ipsilateral rotations during a 30 minute test session or each treatment group. The solid circles/solid lines represent data for animals receiving QA alone, open circles/solid lines represent data for animals receiving QA and NGF secreting BHK cell implants, and solid circles/dashed lines represent data for animals receiving QA and Non-NGF secreting BHK cell implants.

All animals exhibited an increased sensitivity to apomorphine over repeated test sessions. As shown in FIG. 3, QA produced a marked increase in apomorphine-induced rotation behavior. Those animals in the non-NGF group did not differ from animals which received QA alone. However, those animals which received QA together with NGF-secreting BHK cells (see Table IV, QA UNILAT) exhibited a significant attenuation of rotation behavior during all test sessions.

Figure 4A:
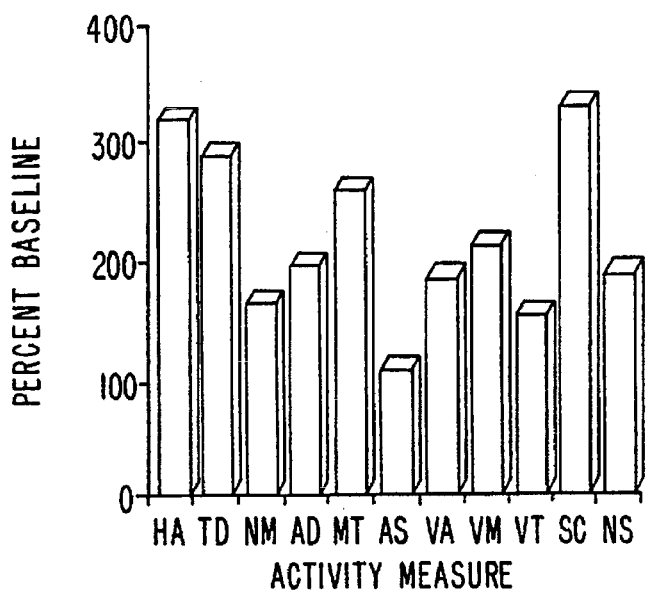
FIG. 4 illustrates the effects of encapsulated NGF-secreting BHK cells on spontaneous locomotor activity in bilaterally lesioned QA rats. Data are presented as the mean (±) SEM percent of presurgery activity levels for each activity measure. In the Figure, HA=horizontal activity, TD=total distance, NM=number of movements, AD=average distance, MT=movement time, AS=average speed, VA=vertical activity, VM=number of vertical movements, VT=vertical time, SC=stereotypy time, and NS=number of stereotypic movements. Panel A-QA; Panel B-2A/Non-NGF; Panel C-QA/NGF.
Figure 4B:
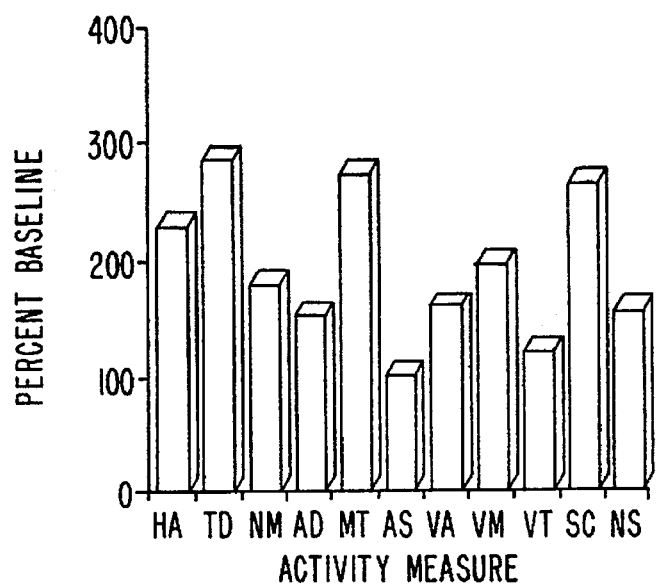
Figure 4C:
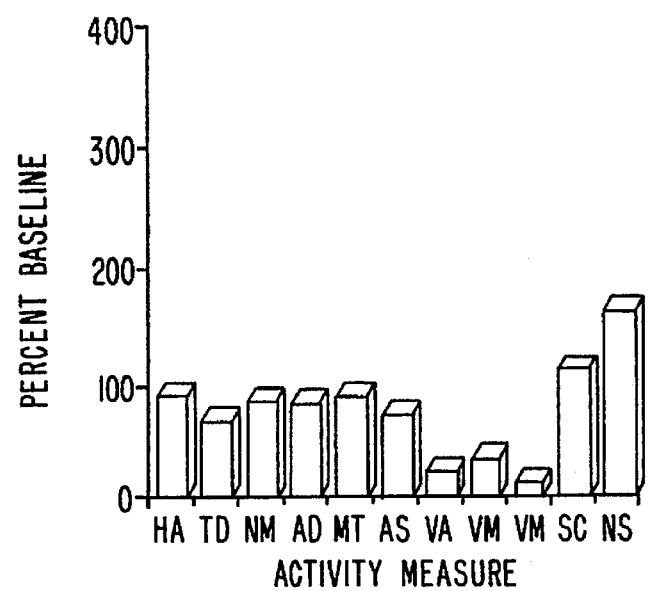

Consistent with the behavior protection observed following unilateral QA, animals exhibited an attenuation of hyperactivity produced by bilateral injections of QA. Animals which received QA alone or QA and non-NGF BHK cell implants (i.e., BHK-controls) exhibited comparable increases in activity which ranged from approximately 100–350% of pre-implant levels (FIG. 4). In contrast, those animals which received QA together with NGF-secreting BHK cells (Table IV, QA BILAT) showed activity levels which were markedly attenuated relative to NON-NGF treated animals and ranged from approximately 25–150% of preimplant values.

Figure 5A:
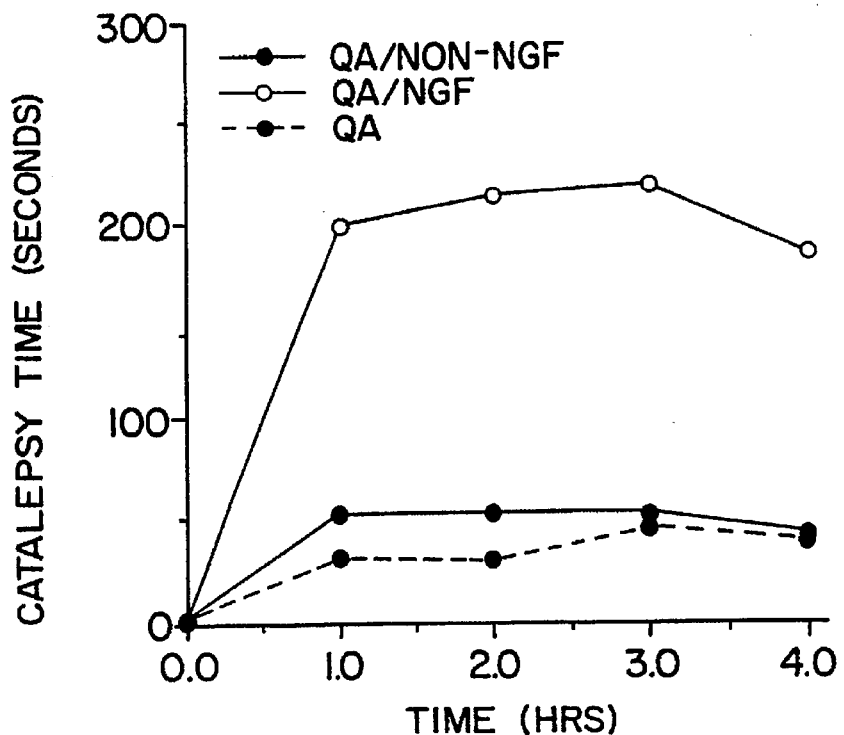
FIG. 5 shows the effects of encapsulated NGF-secreting BHK cells on haloperidol (Panel A) and SCH23390-induced (Panel B) catalepsy in bilaterally lesioned QA rats. Data are presented as the mean (±) amount of time spent in catalepsy for each of the treatment groups. The solid circles/solid lines represent data for animals receiving QA and Non-NGF secreting BHK cell implants, open circles/solid lines represent data for animals receiving QA and NGF secreting BHK cell implants, and solid circles/dashed lines represent data for animals receiving QA alone.
Figure 5B:
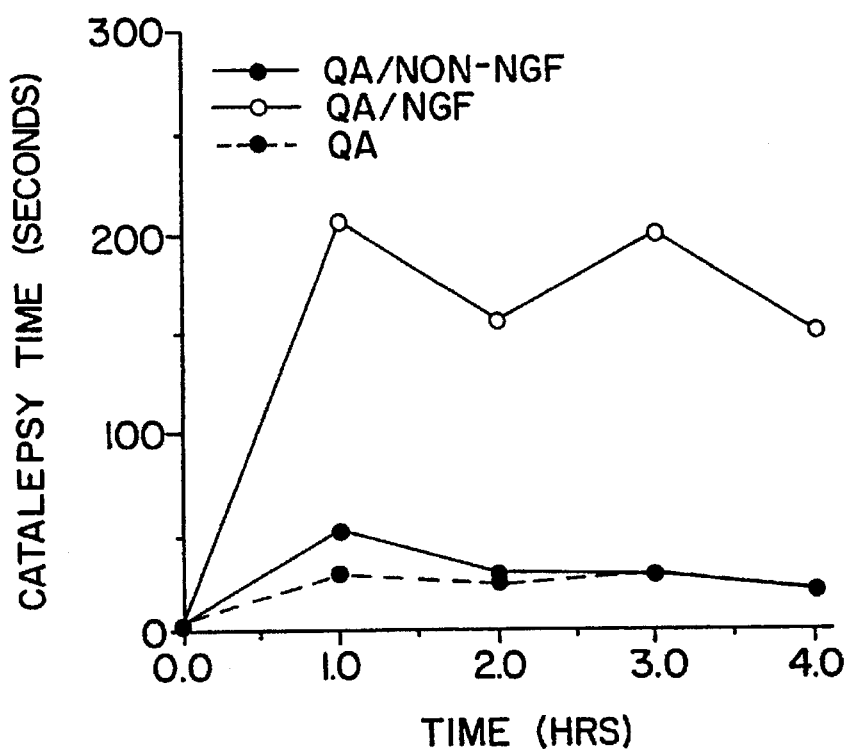

A similar pattern of behavioral protection when the bilateral QA animals were examined for catalepsy. Animals receiving QA alone or in conjunction with non-NGF-secreting BHK cells exhibited catalepsy times ranging from approximately 30–60 seconds in duration following haloperidol and SCH23390 over the 4 hour test period (FIG. 5). In contrast, animals receiving QA and NGF-secreting BHK cells exhibited a robust cataleptic response to both haloperidol (@180–220 seconds) and SCH23390 (@150–220 seconds). Together, these results demonstrate that prior implantation of polymer encapsulated BHK cells are capable of markedly decreasing the behavioral consequences observed following both uni- and bilateral injections of QA.

TABLE IV

± NGF INTO RODENT LESIONED PARADIGMS AS MEASURED BY ELISA IN ng/CAPSULE/24 HR

| Paradigm | Pre- | ±SD | Post- | ±SD |
|---|---|---|---|---|
| QA UNILAT (BHK-NGF) (n = 6) | 34.1 | 6.9 | 16.1 | 6 |
| QA BILAT (BHK-NGF) (n = 8) | 23.7 | 5.5 | 19.8 | 16.1 |
| CONTROLS (BHK-CONTROL) (n = 8) | 0.1 | 0.05 | 0.15 | 0.1 |

B. PRIMATES

The above study was extended to primates.

Four cynomologous monkeys received implanta of XP-11 polymer encapsulated BHK-hNGF cells (as described in Example 1). Four control monkeys received identical encapsulated BHK-control implants lacking the hNGF construct. In each animal, three implants were placed into the head of the caudate nucleus and three implants were placed in the posterior putamen. Coordinates were based upon MRI guidance.

Surgery was performed using standard techniques. Monkeys were anesthetized. Under sterile conditions, a U-shaped incision based on the midline was made exposing the skull overlying the right striatum. A 2 cm×3 cm craniotomy was made overlying the striatum using a high speed drill and the dura was reflected in a U-shaped manner. Three polymer capsule implants were then stereotaxically placed into the head of the right caudate nucleus and three capsules were stereotaxically placed into the right putamen. The tether was cut at the surface of the cortex to facilitate later identification and retrieval. The dura and the skull cap were then reapproximated and sutured back in place. The subcutaneous tissues were sutured with 4-O Coated Vicryl inverted sutures and the skin closed with 4-O Ethilon sutures in routine fashion.

One week following capsule implantation, monkeys received quinolinic acid injections into the caudate nucleus and into the putamen in the immediate vicinity of the capsule implants. Monkeys were videotaped under normal conditions and following apomorphine treatment once per week beginning one week prior to the implant and starting 3 weeks after lesions for two weeks. Just prior to sacrifice, the capsules were removed.

The levels of hNGF release from each capsule will be quantified via ELISA. The biological activity relevance of this hNGF release from the capsule upon retrieval will be assessed via PC12 cell bioassay, and the variability of the implanted BHK cells will be assessed via Nissl staining. The monkey brains will be immunohistologically processed for CHAT, GAD, NADPH, NPY, somatostatin, and Nissl. The area of the lesion will be quantified on Nissl stained sections and the number of ChAT-ir, GAD-ir, NPY-ir, somatostatin-ir, NADPH stained cells will be quantified bilaterally.

EXAMPLE 5: pelivery of NGF into The Human CNS

Recently Olsen et al., *J. Neural Transmission*, 4, pp. 79-95 (1993), described the administration of mouse NGF by intra ventricular infusion using a mini pump system (Medtronic). The infusion system was implanted subcutaneously into the abdominal wall and connected by a subcutaneous catheter to a intraventricular catheter which was inserted through a 2 mm burr hole in the cranium into the right lateral ventricle. A total of 32.4 ml of mouse NGF was infused over a 3 month period.

In a clinical trial using encapsulated BHK cells releasing human NGF from 1-10 XP-11 capsules are stereotaxically placed in the ventricular space located between the septum and caudate or in selected neocortical/hippocampal regions. The capsules release between 50-500 ng of human NGF/24 hours. The capsules will remain implanted for 3-12 months over which time the patients can be monitored for behavioral and biochemical improvements. Patients can be assessed using a series of cognitive function tests including but not limited to: (1) mini-mental state examination, used to assess the level of cognitive functioning (Foistsin et al., *J. Psychiatr. Res.*, 12, pp. 189-198 (1975); (2) Face recognition exam (Backman et al., *Psychol. Aging*, 6, pp. 489-492 (1991); (3) Spatial memory with immediate and delayed (30 min.) testing. Patients can also be monitored with a number of noninvasive methods for verification of cholinergic function and blood flow. Post mortem in vitro studies have demonstrated that cholinergic nicotinic receptors are lost in Alzheimers disease (Nordberg and Winblad, *Neuroscience Lett.*, 72, pp. 115-119 (1986)). Positron emission tomography (PET) can be used to visualize the uptake of $^{11}$C-nicotine as a measurement of nicotinic receptor availability and function. In addition $^{11}$C-butamol can be employed to evaluate cerebral blood flow in various brain regions (Herseovitch et al., *J. Cereb. Blood Flow Metab.*, 7, pp. 527-542 (1987)).

EXAMPLE 6: Delivery of Art Analgesic

The following example illustrates the use of the present invention for the relief of chronic pain in a terminal cancer patient through the use of enkephalin secreting autologous cells. Neural stem cells are generated from a 1 mg biopsy of brain tissue obtained from the subventricular zone of the dorsal lateral aspect of the lateral ventricles from the prospective recipient. A proliferating population of embryonic hippocampal precursor cells is generated from a combination of cerebral cortex, hippocampus, diencephalon, striatum, and/or septum in the presence of bFGF according to the methods of Richards (Richards et al., *Proc. Natl. Acad. Sci. USA*, 89, pp. 8591-8595, (1992)). The proliferating precursor cells are transfected with the pNUT vector containing the enkephalin gens driven from a constitutive promoter such as metallothionein, and selected with methotrexate as described above (see also, e.g., Kaufman et al., U.S. Pat. No. 4,740,461). Successful transformants are identified by their resistance to the selective agent, and expression levels of the heterologous gens are confirmed by radioimmunoassay (RIA).

Approximately 250,000 of the undifferentiated precursor cells are implanted directly into the CSF of the recipient according to the method of Sagen (Sagen et al., U.S. Pat. No. 4,753,635). Following implantation, stem cells cease division within a few cycles of replication and differentiate into enkephalin-expressing glial cells. The continued presence of increased enkephalin in the CSF leads to analgesis in the recipient in a few days to a month.

The above described cells, or alternatively bovine adrenal chromaffin cells, may be encapsulated, for example, in the T1/2 membrane capsules of this invention and implanted in the brain ventricles or sub-arachnoid space of a human.

EXAMPLE 7: Fabrication Of T1/2 Membrane

T1, T2 and T1/2 hollow fiber membranes were fabricated using a coextrusion spinning technique, similar to that described in U.S. Pat. Nos. 5,158,881, 5,284,761 and 5,283,187. Table V shows the characteristics of these T1, T2 and T1/2 membranes. The casting solution for these membranes was 12.5% PAN/PVC (Dynel) in DMSO (w/w). The solution was filtered through a 0.22 μm filter before use. The fibers were spun into a deionized (MilliQ) water bath at 23° C. with deionized (MilliQ) water as the coagulant solution. The nozzle dimensions were: annulus (faceplate) 0.650 mm, capillary 0.475 mm. Polymer flow rates (unitless) were measured on a Gilmont #0 flowmeter (GFO). Coagulant flow rates (unitless) were measured on a Gilmont #4 flowmeter (GF4) (unitless). For T2 and T1/2 membranes the atmosphere in the air gap between the nozzle and the quench bath was humidified in a mist chamber, using a room humidifier. The break strength of the T1/2 fibers of Table V was 19.3±0.5 grams.

These capsules showed reduced tissue ingrowth upon implantation, and 100% retrievability without breakage (10 out of 10).

TABLE V

| | Fiber Type | | |
|---|---|---|---|
| | T1 | T2 | T 1/2 |
| Fiber ID # | HF042293-2 | HF042293-1 | XP11-93-001 |
| Inner Diameter (μm) | 504 ± 8.5 | 480.5 ± 10 | 450 ± 25 |
| Outer Diameter (μm) | 621 ± 11 | 600 ± 13 | 570 ± 30 |
| Hydraulic Permeability (ml/(m² min mmHg)) | 49.5 ± 7 | 38 ± 7 | 53 |
| BSA Rejection (%) | 97 ± 1 | 98.0 ± 0.7 | 88.7 ± 2.1 |
| Ovalbumin Rejection (%) | 68.8 ± 1.5 | 76.3 ± 1.5 | 82.0 ± 1.7 |
| Break strength (gms) | 28.0 ± 0.5 | 28.0 ± 0.5 | 19.3 ± 0.5 |
| Nozzle Height (ins) | 3.5 | 3.5 | 6 |
| Atmosphere | no mist | mist chamber | mist chamber |
| Polymer Flowrate | 30 @ 21 psi GF0 | 28 @ 21 psi GF0 | 27 @ 22 psi GF0 |
| Bore Flowrate | 45 @ 15 psi GF4 | 44 @ 15 psi GF4 | 44 @ 15 psi GF4 |

The T1/2 XP-11 fibers described in Table V had a total macropore area of about 12% of the total outer wall surface area. Approximately 20% of the macropores ranged between 5–10 μm in diameter and about 80% of the macropores were about 10 μm in diameter.

A second T1/2 membrane also produced by coextrusion had an inner diameter of 522.5±10 μm, and an outer diameter of 670±11 μm.

The polymeric casting solution was 12.5% PAN/PVC in NMP (w/w). The bore coagulant solution and the bath was $H_2O$ (MilliQ deionized) at 23° C. The polymer flow rate was 63@25 psi as measured on a Gilmont flowmeter #0. The coagulant flowrate was 69@58 psi as measured on a Gilmont #4 flowmeter. The nozzle annulus (faceplate) diameter was 650 μm. The capillary O.D. was 400 μm; the capillary I.D. was 310 μm. The air gap between the nozzle and the quench bath was 8.0 inches. The atmosphere in the air gap was ambient air (no mist).

The hydraulic permeability was about 35.0 ml/(m² min mmHg). The break strength was 31.0±0.3 grams. These fibers had a total macropore area of approximately 10% of the total outer wall surface area. Greater than 99% of these macropores ranged between 10–15 μm in diameter.

A third T1/2 membrane was fabricated by coextrusion. The polymeric casting solution was 16.0% PAN/PVC (Mw approximately 40K) in NMP (w/w), with 10% $H_2O$. The bore coagulant solution and bath solution was 40% NMP, 60% $H_2O$ at 23° C. The polymer flowrate was 40@28 psi as measured on a Gilmont #0 flowmeter. The coagulant flowrate was 97@15 psi as measured on a Gilmont #4 flowmeter. The nozzle dimensions were: capillary O.D. 400 μm and annulus I.D. 650 μm. The air gap between the nozzle and the quench bath was 10.3 inches. The atmosphere in the air gap was humidified in a mist chamber, using a room humidifier.

The T1/2 fibers had an inner diameter of about 545 μm and an outer diameter of about 639 μm. The hydraulic permeability of these fibers was about 29 ml/(m² min mmHg). The break strength was 29.3±0.5 grams. These fibers had a total macropore area of about 2.4% of the total outer wall surface area. Approximately 17% of the macropores were about 5 μm in diameter, about 33% were about 10 μm in diameter, and about 50% were about 15 μm in diameter.

These T1/2 hollow fibers are asymmetric; they have a dense inner permselective barrier and a large macrovoid trabecular wall structure. The outer surface is only slightly open to host tissue infiltration with the remainder being porous (i.e., not selective) but closed to host tissue ingrowth.

EXAMPLE 8: Improved Cognitive Function In Aged Rats

This study evaluated the potential therapeutic efficacy of encapsulated NGF-producing baby hamster (BHK) cells in a rodent model of dementia. In addition, rats were also tested for evidence of non-cognitive effects of the treatment such as toxicity. For that reason, their pain thresholds were assessed with a hot plate apparatus; and, the rats were examined for evidence of harmful effects with respect to their mortality rates, body weights, and activity levels throughout the day/night cycle.

Cell transfection and culture
1. The cells were produced as described in Example
Cell encapsulation Individual T1/2 (XP1193-001) capsules 7.0±0.5 mm in length were fabricated as described in Example 7. Inner diameters of the capsules ranged in size from 425–500 μm, and the walls were 50–65 μm thick. These membranes had a nominal molecular weight cut-off of approximately 100 kD as measured by dextran convective seiving experiments.

The fiber devices had a septal fixture at the proximal end for cellular loading access and were sealed at the distal end. BHK cells were prepared as a single cell suspension and infused into the septal port at a density of $10^4$ cells per μl after mixing 1:1 with physiologic collagen. After infusing 202.5 μl of the cellular suspension, the septum was removed, and the access port was sealed. BHK cell loaded devices were maintained in PC-1 medium 4–5 days before implantation. After 3 or 4 days, the capsules were rinsed in Hanks' balanced salt solution and placed in 1 ml of fresh PC-1 medium overnight to be analyzed for hNGF by ELISA.

Assessment of Capsule NGF Production

Quantitation of hNGF released from BHK-NGF loaded capsules was performed by a two-site enzyme immunoassay. The protocol was a modification of that described by Boehringer Mannheim using Nunc-Immuno Maxisorp ELISA plates. After color development (30 min), the samples were analyzed on a plate reader and measured against recombinant mouse NGF protein standards. Capsules exhibited a range of hNGF production. In order to ensure that all rats received equivalent amounts of exogenous hNGF, each rat was implanted with one fairly high and one fairly low hNGF-producing capsule.

Rats

Male Fischer 344 rats were purchased from the Harlan Sprague Dawley aging rat colony at the National Institutes of Aging. The older rats were retired breeders. These rats were habituated to the colony room for 1.5 mo before behavioral testing began, and they were maintained throughout their lives on diet NIH-31. On casein-containing diets, the incidence of renal failure in F-344 rats is so high that it makes their use as an animal model of aging questionable. Diet NIH-31 is a soy-protein containing diet that increases longevity and drastically reduces the prevalence of severe chronic nephropathy in ad libitum fed F-344 rats so that renal disease does not confound their use in aging research. See Winn et al., *Proc. Natl. Acad. Sci. USA*, 92, pp. 2324–28 (1994). At the time behavioral testing began the rats were 3.3 mo (n=30), 18.5 mo (n=45), and 24.6 mo (n=60). Ages of the rats in the results are presented as their actual ages during that part of the testing.

Capsule Implantation

Rats were anesthetized with a 1.0 ml/kg im injection of a mixture of ketamine (33 mg/ml), xylazine (1.7 mg/ml), and acepromazine (10 mg/ml). They were positioned in a Kopf stereotaxic instrument, a sagittal incision was made in the scalp and a burr hole drilled at the appropriate coordinates for placement of the polymer capsules into the ventricles. Rats were implanted by placing the capsule within an 18-gauge Teflon catheter mounted to the stereotaxic frame. A stainless steel obdurator was placed within the cannula, the device lowered into the brain, and the obdurator held in place while the outer cannula was raised to passively place the capsule within the lateral ventricles. The stereotaxic coordinates for implantation were: 0.5 mm anterior to bregma, 1.5 mm lateral to the sagittal suture, and 7.5 mm below the cortical surface. Rats not receiving implants were given sham surgeries (anesthetized, scalp lacerated, skull drilled, and dura punctured).

Mortality Rates

The date and general appearance was noted for each rat on the day it died. Mortality date for rats that completed the study were recorded as the perfusion date.

Body Weights

Rats were weighed once each week from the time they arrived in the animal care facility.

Morris water maze

Apparatus: A black fiberglass tank 1.5 m in diameter and 76 cm deep was filled with water (21° C.) to a depth of 32 cm. A square 10 cm×10 cm platform was submerged 0.5 cm below the surface of the water during reference and working memory trials. During cued trials, the platform was marked by a white cylinder (39 cm tall and 1.2 cm in diameter) made of wooden dowels, extending vertically from the platform. A collapsible platform was used for probe trial testing. The SA-3 Tracker with Poly-Track Software (San Diego Instruments, San Diego, CA) was used to track and record the coordinates of the white rat as it moved over the black background. The camera was mounted 178 cm above water level and directed at the center of the tank. The tank was placed against a wall in a room illuminated by two 18 watt fluorescent bulbs and four 50 watt incandescent bulbs positioned around the room below the tank rim. Large 122 cm×183 cm black and white visual cues (checkerboard and bullseye) were placed on opposite walls near the tank.

Reference Memory Testing & Treatment Assignment: The stationary platform was placed halfway between the center and the outside wall of the tank for all trials. Random starting positions throughout the four quadrants were used. Trials were terminated when the rat found the platform or after 2 minutes. At the end of each trial, the rat was placed on the platform for 10 seconds. Prior to surgery, rats underwent one session per day for the first 7 sessions and two sessions per day for the next 8 sessions. Post-surgery, rats underwent one session per day for 5 days, on days 15–19 post-implant.

Post-implant probe Trials: The collapsible platform was placed in the center of the same quadrant used in reference memory trials. The platform was in the down position at the beginning of the trial and raised to the up position after 30 seconds. Random starting positions were used. Trials were terminated when the rat found the platform or after 2 minutes. At the end of each trial, rats were placed on the platform for 10 seconds. Data was collected for the first 30 seconds only. The number of times the rat swam over the platform location during the initial 30 seconds (when the platform was collapsed to the bottom of the tank) were recorded. Rats underwent one trial per day for 5 days on the same days that post-implant reference memory trials were conducted. The order of the probe trials and reference memory trials alternated from one day to the next.

Post-implant Cued Trials: The stationary platform with a black cover secured to the top with rubber bands was placed in the center of the same quadrant used in reference memory testing. Three wooden dowels were taped one on top of the other and attached to the black cover. Random starting positions were used. Rats underwent 3 trials with no intertrial interval after the completion of probe trial testing.

Post-Implant Working Memory Testing: The stationary platform was placed in a new position randomly selected from all 4 quadrants in each session. Random starting positions were used. One session consisted of three trials with no intertrial interval, on four days from day 26 to day 29 post-implant. Another series of working memory Morris water maze tests were conducted with a 2 hr intertrial interval for 6 days from day 30 through day 35 post-implant. Trials were terminated when the rat found the platform or after 2 minutes. At the end of the first two trials, rats were placed on the platform for 10 seconds.

Hot Plate Nociceptive Thresholds

The Hotplate was heated to 50° C. and covered by a Plexiglas box. Rats were placed on the plate and removed immediately when signs of discomfort were displayed (e.g. licking its paws, quick paw flick). The trial was discontinued after 60 seconds, even if no signs of discomfort were displayed. The latency to respond was recorded as the dependent measure. Forty-five days before being implanted, rats were given one trial each day for 5 days, and the means of these 5 trials were computed as a measure of baseline performance. Fifteen days after surgery, another 5 sessions were conducted, one per day. Finally, 35 days postoperatively another session was conducted in the hot plate.

Post-implant Von Frey Hair Somatosensory function

Calibrated Von Frey hairs of 7.37, 12.5 and 20.9 g were used. Rats were placed on a mesh floor (120×45 cm) elevated 45 cm from a table, and covered with a clear plastic cages (24×14×13 cm), and allowed to acclimate for 10 minutes. Yon Frey hairs were pressed against the bottom of the hind paw on the mid-plantar skin until they began to bend, a maximum of 20 times at a frequency of about 2 touches per second. If the rat failed to respond after 20 touches, a value of 21 was assigned. At threshold, rats responded with a quick paw flick, paw withdrawal, or paw lick. Hairs were presented in a random order to the left and right hind paws. Rats underwent one session postoperatively, and the means of the left and right sides were used.

Activity Levels

Rats were placed in a plexiglas cage (42 cm×42 cm×30 cm) with arrays of infrared beams around the perimeter (Integrated Animal Monitoring System, Omnitech Electronics, Inc.) and with a thin layer of beta chips on the bottom from 5:00 pm–9:00 am (lights off from 8:00 pm–8:00 am) before and after implantation. Beam breaks were converted into total distance traveled per hour over the 16 hr sessions.

Data Analyses

Data were analyzed with SAS-PC™. Analyses of variance were conducted using the procedures for general linear models with options for repeated measures where appropriate, and Cronbach's coefficient alpha was computed as the measure of internal reliability (SAS Institute Inc., 1989). Omega squared was computed as a measure of effect size (Dodd and Schultz, Jr., *Psychol. Dull.*, 79, pp. 391–95 (1973)). The SAS-PC PROC LIFETEST procedure, using the product limit method, was used to estimate survival distributions according to strata. The log-rank test was used to test for equality of survival between the strata. Except for mortality rates, all data reported and analyzed was restricted to those subjects that survived to the end of the study.

Capsule hNGF Production

All 14 encapsulated BHK-control cells (from non-transfected controls) had 0ng/20 hr NGF output at the time of explant. There were 43 rats implanted bilaterally with BHK-NGF capsules that survived to the end of the study. hNGF production from encapsulated BHK-NGF capsules ranged from 0.80 ng/20 hr to 17.4 ng/20 hr preimplant, and from 0.00 ng/20 hr to 12.1 ng/20 hr post-explant. The sum of the hNGF output from the two capsules for each animal before implantation was 11.5±0.56 ng/20 hr, and declined to 7.3±0.75 ng/20 hr when measured post-explant. Neither the sum of hNGF output from the two capsules before implantation or after explanation was correlated with performance in any of the water maze tests.

Mortality Rates

At the time the rats arrived in the animal care facility they were 1.8 mo (n=30), 17 mo (n=45), and 23.1 mo (n=60). None of the youngest rats, seven of the 45 middle aged rats (15%), and 18 of the 60 oldest rats (30%), died between the time they arrived in the animal care facility and the time they were scheduled for surgery approximately 65 days later.

None of the rats at any age died during surgery or recovery from the anesthetic. None of the young rats, 1 of the 18 middle-aged rats implanted with encapsulated BHK-NGF cells (5.5%), 4 of the 20 oldest control rats (20%), and 6 of the 22 oldest rats implanted with encapsulated BHK-NGF cells (27%), died between the time they were implanted and the time they were scheduled to be euthanized approximately 40 days later.

The number of survivors and their ages at the time the rats were euthanized were: 5.4 mo (n=30), 20.6 mo (n=37), and 26.7 mo (n=32), respectively, for a total N=99 rats that survived to the end of the study. Only the data from those 99 survivors was included in the analyses of the data sets reported below.

Body Weights

The youngest rats had the lowest body weights, the middle-aged rats were the heaviest and the oldest rats were intermediate in weight. Age accounted for a large proportion of the variance in the data, $\omega^2=0.89$, $F(2,81)=722.6$, $p=0.0001$. Body weights changed significantly over the 8 weeks before surgery. The youngest rats continued to gain weight, while the middle-aged and oldest rats continuously lost weight. The rats were assigned to groups based on their pre-implant performance in the reference memory version of the Morris water maze, not on the basis of pre-implant body weight. Consequently, among the middle-aged rats, the rats scheduled to be implanted with encapsulated BHK-NGF cells were not quite as heavy (before they were implanted) as the rats assigned to the control groups.

Body weights changed over the 4 weeks after surgery. The youngest rats continued to gain weight while the middle-aged and oldest rats continued to lose weight after implantation/sham surgery. Post-hoc contrasts showed that rats implanted with encapsulated BHK cells were significantly lighter than the controls given sham surgeries, $F(1,81)=8.34$, $p=0.005$, while the rats implanted with encapsulated BHK-NGF cells were no lighter than the rats implanted with encapsulated BHK cells, $F(1,81)=0.07$, $p=0.79$. Means of post-implant body weights show that the sham implanted rats were 386.8±9.3 g, while body weights of the rats implanted with encapsulated BHK cells were 3% less (375.5±11.0 g), and the body weights of the rats implanted with encapsulated BHK-NGF cells were 2% less than the sham implanted group (379.8±6.5 g). Even in terms of proportion of variance accounted for, the effects of treatment on body weights were small. Furthermore, there was no evidence that either the rate or pattern of change in body weights was influenced by treatment over the 4 weeks after implantation.

Activity Levels

Total distance traveled for each hour over a 16 hr period from 5:00 pm–9:00 am (lights off from 8:00 pm–8:00 am) shows that pre-implant activity levels were high initially and declined, but increased dramatically when the lights went out during the 4th hour in the boxes. Younger rats were more active than older rats. Activity levels were also affected significantly by time of day.

The main effect for treatment was statistically significant on post-implant activity levels, $F(2,81)=4.32$, $p=0.017$. Post-hoc analyses of post-implant activity levels for each age group shows that there was a significant effect of Treatment (BHK-NGF implants) among the 3.3 mo rats, $F(2,24)=4.18$, $p=0.027$. The main effect for Treatment was not significant among the middle-aged rats, $F(2,31)=1.92$, $p=0.16$, or among the oldest rats, $F(2,26)=2.12$, $p=0.14$.

Hot Plate

NGF delivered by the encapsulated, intraventricular BHK-NGF cells did not appear to affect latencies to respond to the hot plate. The main effect of Treatment was not statistically significant, $F(1,87)=0.03$, $p=0.865$.

von Frey Hair Somatosensory Thresholds

Figure 6A:
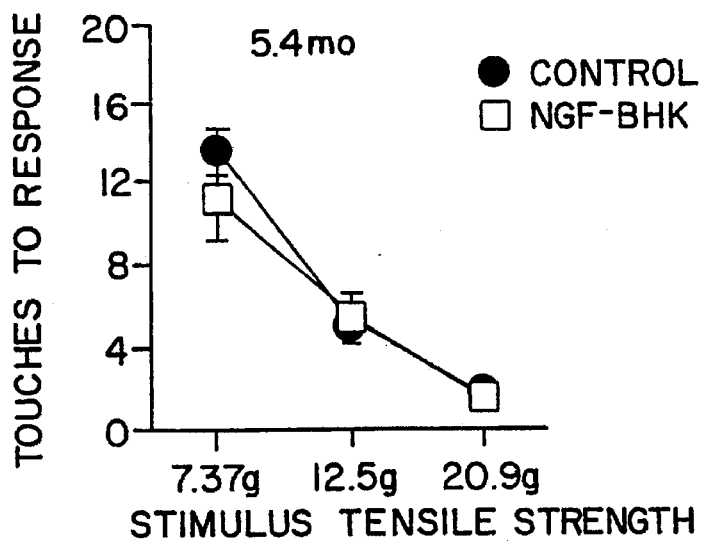
FIG. 6 depicts von Frey Somatosensory Thresholds, measured by touches to response at each of three tensile strengths. Panel A-5.4 mo; Panel B-20.6 mo.; Panel C-26.7 mo. Old rats (26.7 mos.) implanted with encapsulated BHK-NGF cells were more responsive to the light stimulus than old rats in the control groups, but they were no more responsive than the young rats. Closed circles represent controls; squares represent NGF-BHK cell data.
Figure 6B:
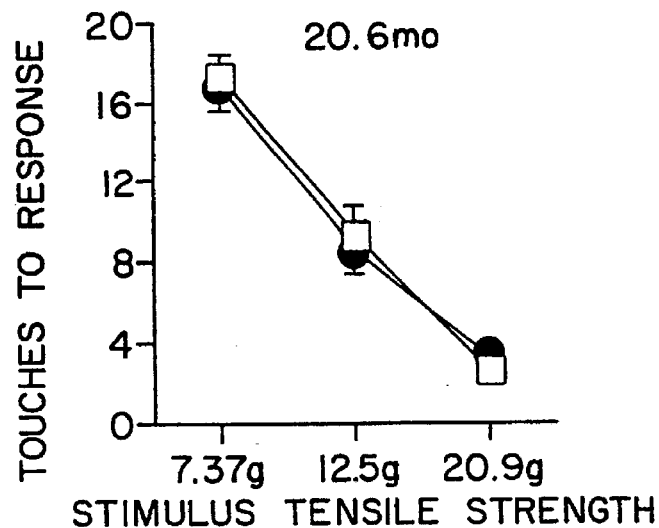
Figure 6C:
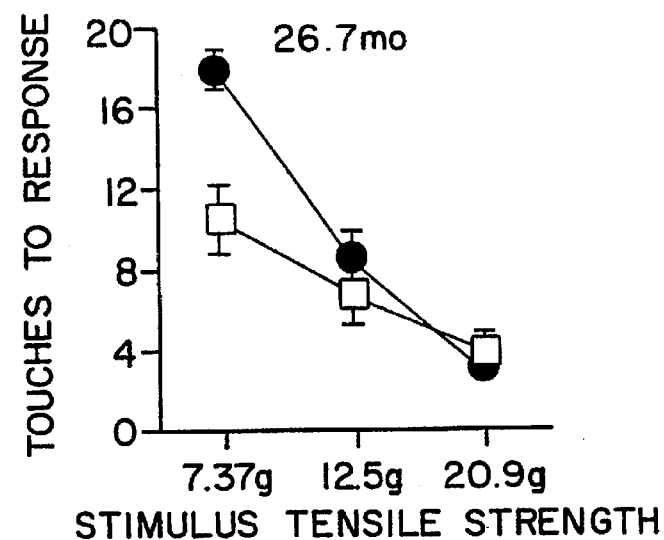

Rats responded more quickly to the stiffer von Frey hairs. Younger rats also tended to respond more quickly than older rats. Exogenous NGF affected performance among the older rats on the lighter stimulus, but not the younger groups. However, the oldest rats receiving exogenous NGF were not more responsive than the young rats (FIG. 6).

Spatial learning Morris Water Maze

Pre-implant Reference memory Morris water maze performance:

The distance of the pre-implant swim path to the platform declined for all groups over the 11 days of initial testing. Older rats were more impaired than younger rats. There was a fairly large range in performance at all ages. Animals were assigned to treatment groups by matching them according to their performance in the pre-implant reference memory Morris water maze and there were no significant differences between treatments before being implanted.

Post-implant reference memory Morris water maze: There were no differences between the two control groups in terms of their performance in the post-implant reference memory version of the Morris water maze so those two groups, the group implanted with encapsulated non-transfected BHK cells, and the group receiving the sham surgery were combined into a single control group. Swim distance did not decline beyond distances reached at the end of pre-implant acquisition.

There were differences in performance between the different age groups. Encapsulated BHK-NGF cells did not have a statistically significant effect on performance. Rats performing among the better 50% and worse 50% in pre-implant reference memory Morris water maze were significantly different in these post-implant trials.

Post-implant probe Trials: There were no differences between the two control groups in terms of their performance in the post-implant Morris water maze probe trials so the group implanted with encapsulated non-transfected BHK cells, and the group receiving the sham surgery were combined into a single control group. Younger rats crossed over the platform location more frequently during the first 30 s of swim time than older rats. The BHK-NGF cells did not produce a statistically significant effect.

Working memory Morris water maze with 0 ITI: From 26–29 d after surgery, the rats were tested 3 trials per day in a working memory version of the Morris water maze. The platform was moved each day to a randomly selected location throughout the pool, including different distances from the wall of the pool. There was no delay between trials (0 ITI). Performance over the 4 days was averaged for trials one, two, and three. There were no differences between the BHK and sham surgery control groups so those groups were combined into one control group. Performance improved consistently across the three trials. The pattern of improvement over trials was different for older rats than for younger rats. NGF supplied by the encapsulated BHK-NGF cells did not have a statistically significant effect in this task.

Figure 7A:
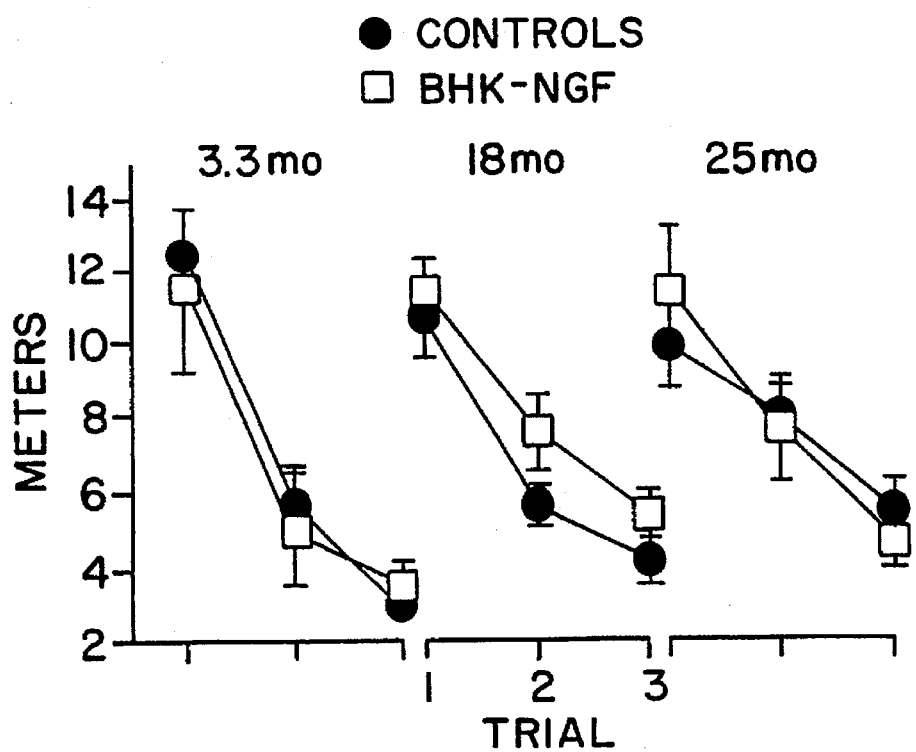
FIG. 7 shows the results of a working memory version of the Morris water maze test, with a two hour interval between trials. Panel A-Better 50% Pre-implant; Panel B-Worse 50% Pre-implant. Closed circles represent controls; squares represent NGF-BHK cell data.
Figure 7B:
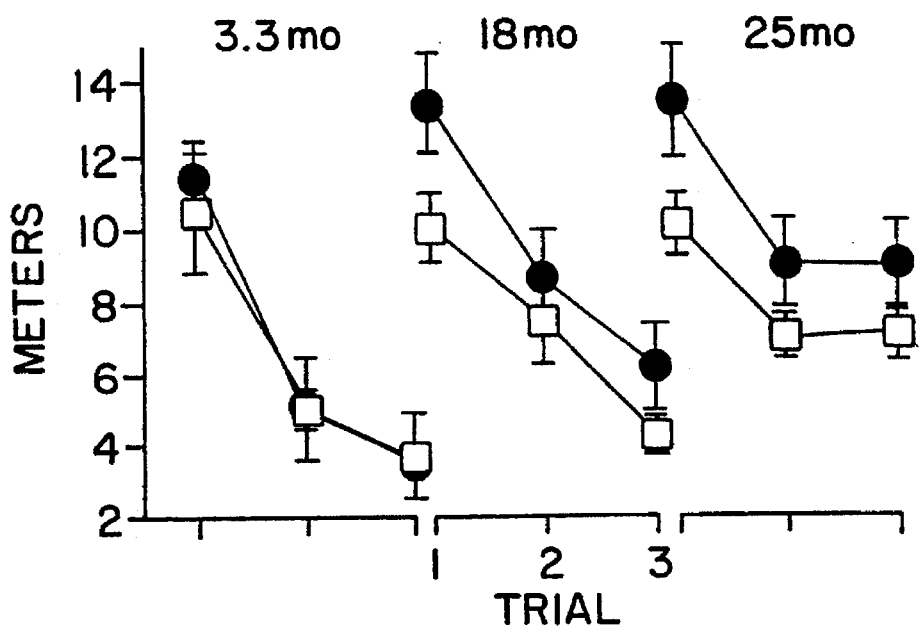

Working memory Morris water maze with 2 hr ITI: From 30–35 d after surgery, the rats were tested 3 trials per day in a working memory version of the Morris water maze. The platform was moved each day to a randomly selected location throughout the pool, including different distances from the wall of the pool. There was a 2 hr interval between trials, during which the rats were dried and warmed for 15 min under an infrared heat lamp before being returned to their home cages. Performance over the 6 days was averaged for trials one, two, and three (FIG. 7). There were no differences between the BHK and sham surgery control groups so those groups were combined into one control group.

Performance improved consistently across the three trials. Younger animals generally performed better than older rats.

The performance of rats implanted with encapsulated BHK-NGF cells that had been performing more poorly before surgery, was better than the poor performers in the control group (FIG. 7).

These results suggest that CNS-implanted semipermeable membranes, containing genetically-modified xenogeneic cells continuous produce hNGF that attenuate age-related cognitive deficits in nonimmunosuppressed rats, and that both the surgical implantation procedure and long-term exposure to low doses of hNGF appear safe.

EXAMPLE 9: Implantation of Encapsulated BHK-NGF Cells In Fornix Lesioned Aged Monkeys The present study demonstrates that grafts of polymer-encapsulated cells which have been genetically modified to secrete human NGF (hNGF) can prevent the degeneration of axotomized CBF neurons in aged monkeys and these grafts induce the sprouting of cholinergic fibers proximal to the implants.

Six female Rhesus monkeys (Macaca mullata) between the ages of 24–29 years of age (equivalent to about 75–87 years of age in humans) were employed in this study. All monkeys received unilateral lesions of the left fornix. Monkeys were anesthetized with isoflurane (1.5–2.0%). Following pretreatment with mannitol (0.25 g/kg, iv) unilateral transections of the left fornix were performed (J. H. Kordower, M. S. Fiandaca, *J. Comp. Neurol.*, 298, pp. 443 (1990). A surgical drill was used to create a parasagittal bone flap (size=1.5 cm×4.0 cm) which exposed the frontal superior sagittal sinus. The dura was retracted and a self-retaining retractor used to exposer the interhemispheric fissure. The corpus callosum was longitudinally incised. At the level of the foramen of Monro, the fornix is easily visualized as a discrete 2–3 mm wide white fiber bundle. The fornix was initially transected using a ball dissector. The cut ends of the fornix were then suctioned to ensure completeness of the lesion.

Immediately thereafter, each monkey received implants of XP-11 polymer capsules into the left lateral ventricle which contain baby hamster kidney (BHK) fibroblasts that were (n=3) or were not (n=3) genetically modified to secrete hNGF (as described in Example 1). Individual BHK cell-containing XP-11 capsules were manually placed within the lateral ventricle with fine forceps between the head of the caudate and the septal nucleus. A total of 5 devices were implanted in each animal oriented in a row in the rostro-caudal direction. The capsules abutted the caudate and septum, remained upright, and did not require to be secured further. The dura was reapproximated, the bone flap was sutured back in place and the galea and skin was sutured using routine methods.

All monkeys were sacrificed 3–4 weeks postimplantation and processed for the histochemical visualization of acetylcholinesterase (ACHE; Hedreen et al., *Cytochem.*, 33, p. 134 (1985)) and the immunohistochemical visualization of choline acetyltransferase (CHAT), low affinity NGF receptor (p75 NGFr), dopamine β-hydroxylase (DBH) and β amyloid. Animals were replaced into the sterotaxic frame, the previously prepared bone flap was removed, the cerebral hemisphere retracted and the BHK cell-loaded capsules removed. Immediately following removal of the capsules, animals were transcardially perfused with phosphate-buffered saline (pH=7.4) followed by fixation with 3.5 liters of a 4% Zamboni's fixative. Frozen sections were cut (40 µm) on a sliding knife microtome. Every third section through the septal/diagonal bank complex was processed immunocytochemically for CHAT (1:7,500; Chemicon), the p75 NGF receptor (1:80,000; Dr. Mark Bothwell), or A4 (1:1,000; Dr. Dennis Selkoe) using previously described procedures (e.g. J. H. Kordower and Fiandaca, supra; Kordower et al. *J. Comp. Neurol.* 277, p. 465, (1988)). Counts of cholinergic neurons within the medial septum were performed manually. The number of CHAT- and p75 NGFr-ir neurons within the medial septum were quantified bilaterally from a minimum of 5 sections matched for level per animal. The number of cholinergic neurons was compared across groups using a two-tailed students T-test.

Beginning post-operatively and continuing for the duration of the experiment, monkeys receiving NGF-secreting transplants appeared lethargic relative to control grafted monkeys. Each monkey displayed numerous β amyloid-immunoreactive plaque-like structures within the temporal and parietal neocortex, the amygdala and hippocampus. NGF administration had no effect on the number or distribution of amyloid plaques in comparison to control animals (data not shown). Nissl and AChE-stained sections through the lesion site revealed that the left fornix was transacted in all animals at the level of the caudal foramen of Monro resulting in a comprehensive loss of AChE-containing fibers within the ipsilateral hippocampus relative to the intact contralateral side.

Figure 8:
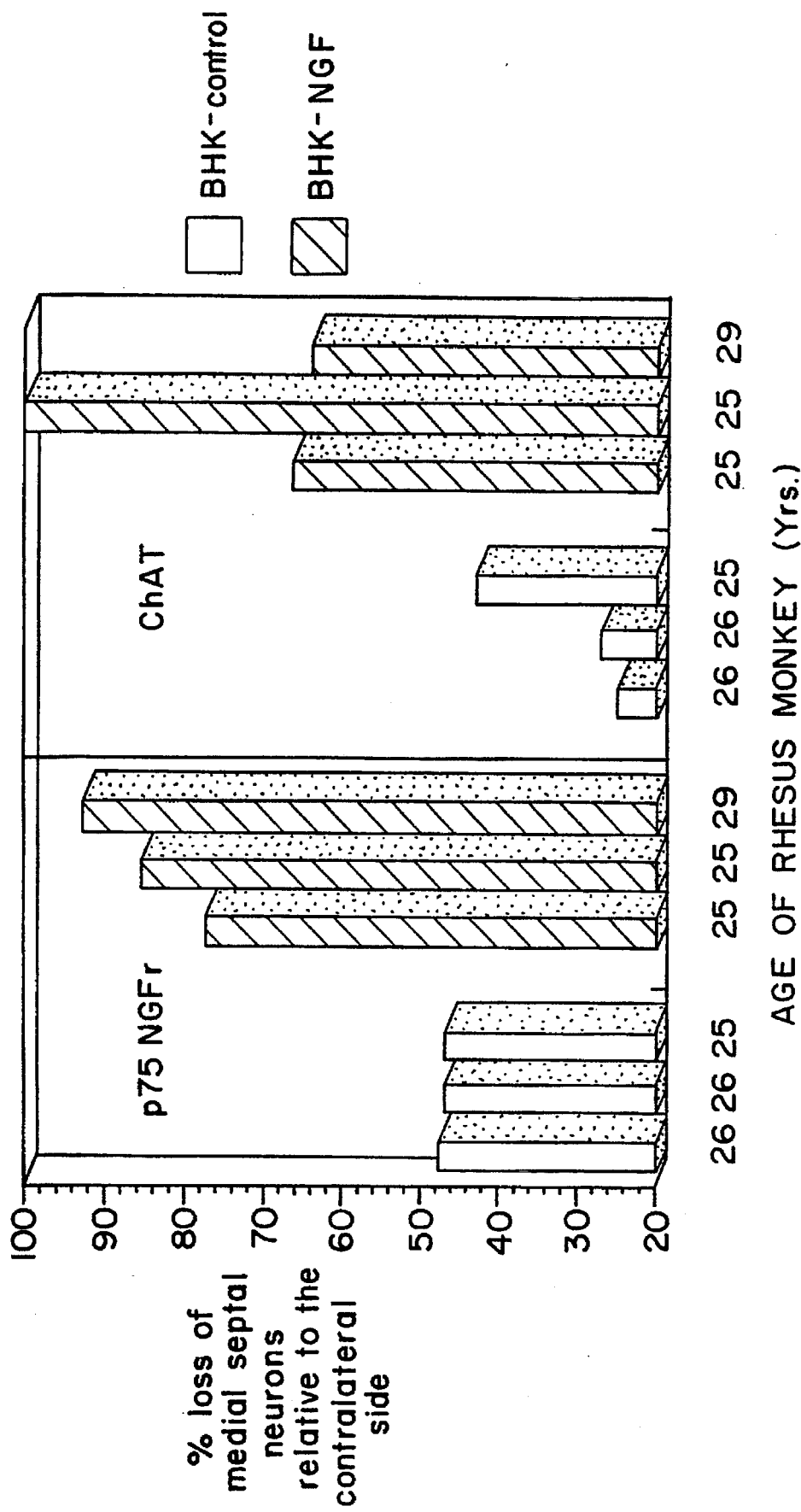
FIG. 8 shows that in aged monkeys receiving encapsulated BHK-NGF cells, lesion-induced degeneration of septal neurons was significantly attenuated compared to controls.

Monkeys receiving BHK-control grafts displayed a significant reduction of ChAT (57%–75%) and p75 NGFr-ir (52%–53%) neurons within the medial septum ipsilateral to the transplant (FIG. 8). Many remaining neurons within the septum appeared atrophic relative to ChAT- and p75 NGFr-ir septal neurons on the contralateral side. The lesion-induced degeneration of septal neurons was significantly attenuated in monkeys receiving grafts of polymer-encapsulated BHK-hNGF cells as these monkeys displayed only a 0–36% reduction in ChAT ($p<0.001$) and a 7–23% reduction in p75 NGFr-ir neurons ($p<0.001$) within the medial septum ipsilateral to the lesion relative to the contralateral side (FIG. 8).

In addition to maintaining the viability and continued expression of the cholinergic phenotype in septal neurons, the BHK-hNGF grafts induced a robust sprouting of cholinergic fibers within the ipsilateral septum. All monkeys receiving BHK-hNGF grafts displayed a plexus of p75-

NGFr-ir fibers within the lateral aspect of the septum proximal to the grafts. These fibers ramified against the ependymal lining of the lateral ventricle. In contrast, none of the BHK-control grafted monkeys displayed a cholinergic sprouting response. These fibers were also ChAT-ir and AChE-positive confirming the cholinergic phenotype of this sprouting response. In one case, the BHK-hNGF capsule penetrated the lateral ventricle ventrally, lodging within the parenchyma of the rostral basal forebrain. A focal plexus of p75 NGFr-ir fibers was observed proximal to this implant site. While a few fibers originating from the posterior septum and the posterolateral portion of the vertical limb of the diagonal band appeared to contribute to this fiber plexus, the precise cells of origin giving rise to this fiber plexus remains to be established. What is clear is that these fibers are not derived from the sympathetic nervous system since they were thin, varicose, and not immunoreactive for DBH. Interestingly, an occasional p75 NGFr-ir neuron was seen within the fiber plexus but these cells were too few in number to contribute significantly to this fiber system.

Prior to implantation, analysis by ELISA indicated that the BHK-hNGF grafted monkeys received capsules producing a total of 44.65±0.95 ng NGF/24 h per animal. At the time of retrieval just prior to sacrifice, numerous Nissl stained BHK cells were observed within the capsules which now produced hNGF at a rate of 9.6 ng/24 h per animal. Media obtained from these capsules following grafting for one month in aged monkeys induced a robust differentiation of PC12A cells in vitro indicating that this level of NGF production was biologically relevant.

This study is the first demonstration that NGF can provide trophic and tropic influences to degenerating cholinergic basal forebrain (CBF) neurons in the aged primate brain. The trophic and tropic effects presently observed can be attributed to graft-derived hNGF with a high degree of certainty since the treatment strategies in the two groups of monkeys, receiving BHK-hNGF and BHK-control grafts respectively, differed exclusively by the single gene encoding the synthesis of hNGF. When axotomized, a consistent degeneration of CBF neurons was observed in control grafted monkeys. In contrast, implants of polymer capsules containing BHK cells genetically modified to secrete hNGF prevented the degeneration of damaged cholinergic medial septal neurons.

CBF neurons are the only cells in the brain shown to express both the low affinity p75 NGF receptor and the high affinity trk A receptor (Steininger et al., *Brain Res.*, 612, pp. 330 (1993)). Interestingly, the present study also revealed a partial discordance in the expression of these two cholinergic markers in response to axotomy in the aged animals with the expression ChAT being more sensitive than the p75 NGFR to the effects of the lesion. Since the expression of ChAT and the p75 NGFR is usually highly concordant this suggests that septal neurons in monkeys are still viable following axotomy but are not expressing detectable levels of cholinergic markers.

Furthermore, implants of hNGF-secreting capsules induced a robust sprouting of cholinergic fibers proximal to the implant. Importantly, both the trophic and tropic effects of the hNGF-secreting grafts were observed in the 29 year old monkey. These data suggests that CBF neurons in the aged primate are responsive to hNGF for their lifetime.

This data also suggests that relatively low levels (ng/day) of hNGF may suffice in supporting degenerating basal forebrain neurons.

The present study demonstrates the feasibility of grafting encapsulated cells which have been genetically modified to secrete hNGF to the aged primate brain. This encapsulation procedure permits the use of xenografts without the need for potentially toxic treatments employing drugs which suppress the immune system. The encapsulated cells were well tolerated in the present study and only a minimal astrocytosis was observed proximal to the implants. BHK cells remained viable within the capsules and produced detectable and biological levels of hNGF for the duration of the experiment.

EXAMPLE 10: Implantation of Encapsulated BHK-NGF Cells And Unencapsulated Adrenal Chromaffin Cells In Hemiparkinsonian Rats NGF-secreting BHK cells were prepared and encapsulated substantially as described in Example 8. Hemiparkinsonian rats received unencapsulated adrenal chromaffin cell grafts into the left lateral ventricle or into the left striatum. Some rats also were received encapsulated NGF-BPFK cells implanted into the left lateral ventricle or into the left striatum in both cases 1.5 mm away from the adrenal medullary chromaffin cells.

Although the animals receiving chromaffin cells alone or chromaffin cells with intraventricular hNGF-secreting devices did not show recovery from apomorphine-induced rotational behavior, the animals receiving chromaffin cells with intrastriatal hNGF-secreting cell implants showed a significant reduction in rotational behavior 2 and 4 weeks after transplantation.

Histological analysis revealed that in animals receiving chromaffin cells and an intraventricular hNGF-secreting device, there was an approximately 5–6 fold increase in chromaffin cell survival (TH-IR) when compared to animals receiving chromaffin cells alone.

In those animals receiving chromaffin cell grafts together with intrastriatal hNGF-secreting devices, the number of surviving chromaffin cells that were TH-IR was more than 20 times higher than in animals receiving adrenal medullary cells alone. Analysis of retrieved capsules revealed that hNGF continued to be released by encapsulated BHK-hNGF cells after 4 weeks in vivo. These results indicate the potential use of intrastriatal implantation of encapsulated hNGF-secreting cells for augmenting the survival of cografted chromaffin cells.

We claim:

1. A capsule comprising a semipermeable membrane, the membrane comprising an inner wall surface that is permselective, an outer non-permselective wall surface, and a trabecular wall therebetween, the outer wall surface containing macropores, the macropores comprising between about 2.0–20% of the total area of the outer wall surface, and ranging from about 5–15 μm in diameter.

2. The capsule of claim 1, wherein the capsule is shaped to form a cylindrical hollow fiber.

3. The capsule of claim 2 wherein the capsule is shaped to form a flat sheet.

4. The capsule according to any one of claims 1–3, wherein the macropores comprise about 2.5% of the total area of the outer wall surface.

5. The capsule according to any one of claims 1–3 wherein the macropores comprise about 10% of the total area of the outer wall surface.

6. The capsule according to any one of claims 1–3 wherein the macropores comprise about 12% of the outer wall surface.

* * * * *